United States Patent
Rivas et al.

(10) Patent No.: US 10,458,982 B2
(45) Date of Patent: Oct. 29, 2019

(54) FLUIDIC DEVICE INCLUDING BAW RESONATORS ALONG OPPOSING CHANNEL SURFACES

(71) Applicant: Qorvo US, Inc., Greensboro, NC (US)

(72) Inventors: Rio Rivas, Bend, OR (US); Kevin McCarron, Bend, OR (US)

(73) Assignee: QORVO US, INC., Greensboro, NC (US)

( * ) Notice: Subject to any disclaimer, the term of this patent is extended or adjusted under 35 U.S.C. 154(b) by 370 days.

(21) Appl. No.: 15/337,429

(22) Filed: Oct. 28, 2016

(65) Prior Publication Data

US 2017/0122936 A1 May 4, 2017

Related U.S. Application Data

(60) Provisional application No. 62/248,392, filed on Oct. 30, 2015.

(51) Int. Cl.
*G01N 33/543* (2006.01)
*G01N 29/02* (2006.01)
(Continued)

(52) U.S. Cl.
CPC .... *G01N 33/5438* (2013.01); *B01L 3/502707* (2013.01); *B01L 3/502715* (2013.01);
(Continued)

(58) Field of Classification Search
USPC ............ 73/61.45, 61.49, 61.75, 61.79, 64.53
See application file for complete search history.

(56) References Cited

U.S. PATENT DOCUMENTS

| 4,640,756 A | 2/1987 | Wang et al. |
| 6,320,295 B1 | 11/2001 | McGill et al. |

(Continued)

FOREIGN PATENT DOCUMENTS

| DE | 10 2006 004 448 B3 | 10/2007 |
| WO | WO 2006/063437 A1 | 6/2006 |

(Continued)

OTHER PUBLICATIONS

Qorvo US, Inc., "Summary of Sales Activity of Predecessor to Applicant Concerning Tilted C-Axis Aluminum Nitride Products," Unpublished, Jan. 10, 2017, 1 page.

(Continued)

*Primary Examiner* — Daniel S Larkin
(74) *Attorney, Agent, or Firm* — Mueting, Raasch & Gebhardt, P.A.

(57) ABSTRACT

Multiple bulk acoustic wave (BAW) resonator structures are arranged along opposing surfaces of a fluidic passage arranged to receive a fluid. At least one resonator structure may be overlaid with functionalization (e.g., specific binding or non-specific binding) material to bind one or more analytes contained in the fluid. Combinations of BAW resonators providing dominant shear response for detection, and providing dominant longitudinal response for mixing or analyte movement, may be provided on one or more surfaces bounding a fluidic passage. Embodiments may reduce the footprint of multi-resonator fluidic device, enhance analyte binding rate, and/or enhance mixing of sample constituents.

20 Claims, 7 Drawing Sheets

(51) Int. Cl.

| | |
|---|---|
| G01N 29/22 | (2006.01) |
| H03H 9/205 | (2006.01) |
| B01L 3/00 | (2006.01) |
| G01N 29/036 | (2006.01) |
| H03H 9/17 | (2006.01) |

(52) U.S. Cl.
CPC ...... *B01L 3/502761* (2013.01); *G01N 29/022* (2013.01); *G01N 29/036* (2013.01); *G01N 29/222* (2013.01); *H03H 9/205* (2013.01); *B01L 2200/12* (2013.01); *B01L 2300/0645* (2013.01); *B01L 2300/0887* (2013.01); *G01N 2291/0255* (2013.01); *G01N 2291/0256* (2013.01); *G01N 2291/0426* (2013.01); *G01N 2291/106* (2013.01); *G01N 2610/00* (2013.01); *H03H 9/175* (2013.01)

(56) References Cited

U.S. PATENT DOCUMENTS

| | | | |
|---|---|---|---|
| 7,468,608 | B2 | 12/2008 | Feucht et al. |
| 7,802,466 | B2 * | 9/2010 | Whalen ............. B01L 3/502776 73/54.41 |
| 8,409,875 | B2 | 4/2013 | Johal et al. |
| 9,096,823 | B1 | 8/2015 | Branch et al. |
| 2006/0054941 | A1 | 3/2006 | Lu et al. |
| 2006/0125489 | A1 | 6/2006 | Feucht et al. |
| 2006/0222568 | A1 | 10/2006 | Wang et al. |
| 2007/0210349 | A1 | 9/2007 | Lu et al. |
| 2010/0088039 | A1 | 4/2010 | Yang et al. |
| 2015/0293060 | A1 | 10/2015 | Jacobsen |
| 2017/0110300 | A1 | 4/2017 | McCarron et al. |
| 2017/0120242 | A1 | 5/2017 | Rivas et al. |
| 2017/0122911 | A1 | 5/2017 | McCarron et al. |
| 2017/0134002 | A1 | 5/2017 | Rivas et al. |

FOREIGN PATENT DOCUMENTS

| | | |
|---|---|---|
| WO | WO 2007/123539 A1 | 11/2007 |
| WO | PCT/US2016/059312 | 10/2016 |
| WO | PCT/US2016/059327 | 10/2016 |
| WO | PCT/US2016/059677 | 10/2016 |
| WO | WO 2017/075344 A1 | 5/2017 |
| WO | WO 2017/083131 A1 | 5/2017 |

OTHER PUBLICATIONS

Chen, Ying-Chung et al., "The Liquid Sensor Using Thin Film Bulk Acoustic Resonator with C-Axis Tilted AlN Films," Journal of Nanomaterials, vol. 2013, Article ID 245095, 2013, 8 pages.

Corso, Christopher et al., "Development of a Simple Inexpensive Bulk Acoustic Wave (BAW) Nanosensor for Cancer Biomarkers: Detection of Secreted Sonic Hedgehog from Prostate Cancer Cells," Abstract #8866, Winship Cancer Institute, Emory University, Georgia Institute of Technology, Oct. 2012, 1 page.

Groner, M. D. et al., "Gas diffusion barriers on polymers using $Al_2O_3$ atomic layer deposition," Applied Physics Letters, vol. 88, Jan. 31, 2006, pp. 051907-1 to 051907-3.

Lee, Chia-Yen et al., "Microfluidic Mixing: A Review," International Journal of Molecular Sciences, vol. 12, May 18, 2011, pp. 3263-3287.

Link, Mathias, "Study and realization of shear wave mode solidly mounted film bulk acoustic resonators (FBAR) made of c-axis inclined zinc oxide (ZnO) thin films: application as gravimetric sensors in liquid environments," Université Henri Poincaré—Nancy I, Thesis, Sep. 14, 2006, 225 pages.

Meyer, Jens et al., "$Al_2O_3/ZrO_2$ Nanolaminates as Ultrahigh Gas-Diffusion Barriers—A Strategy for Reliable Encapsulation of Organic Electronics," Advanced Materials, vol. 21, 2009, pp. 1845-1849.

Milyutin, Evgeny, "Theoretical and Experimental Study of Piezoelectric Modulated AlN Thin Films for Shear Mode BAW Resonators," EPFL, Thesis No. 5113, Nov. 4, 2011, 109 pages.

Munir, Farasat, "A Fast, Scalable Acoustic Resonator-Based Biosensor Array System for Simultaneous Detection of Multiple Biomarkers," Thesis, Georgia Institute of Technology, Dec. 2012, 160 pages.

Nirschl, Martin et al., "CMOS-Integrated Film Bulk Acoustic Resonators for Label-Free Biosensing," Sensors, vol. 10, No. 5, Apr. 27, 2010, pp. 4180-4193.

Yu, Hongyu et al., "Ultra Temperature-Stable Bulk-Acoustic-Wave Resonators with $SiO_2$ Compensation Layer," IEEE Transactions on Ultrasonics, Ferroelectrics, and Frequency Control, vol. 54, No. 10, Oct. 2007, pp. 2102-2109.

Zhou, Yan et al., "Interfacial Structures and Properties of Organic Materials for Biosensors: An Overview," Sensors, vol. 12, Nov. 6, 2012, pp. 15036-15062.

U.S. Appl. No. 62/247,233, filed Oct. 28, 2015, Rivas.
U.S. Appl. No. 62/248,392, filed Oct. 30, 2015, Rivas.
U.S. Appl. No. 62/252,688, filed Nov. 9, 2015, Rivas.
U.S. Appl. No. 15/293,063, filed Oct. 13, 2016, McCarron et al.
U.S. Appl. No. 15/337,338, filed Oct. 28, 2016, Rivas et al.
U.S. Appl. No. 15/339,062, filed Oct. 31, 2016, Rivas et al.
U.S. Appl. No. 15/339,022, filed Oct. 31, 2016, McCarron et al.

Author unknown, "Acoustic Wave Sensors," Vectron International, Date Unknown, 44 pages, <www.sengenuity.com/tech_ref/AWS_WebVersion.pdf>.

Bjurström et al., "Design and Fabrication of Temperature Compensated Liquid FBAR Sensors," IEEE Ultrasonics Symposium, (IEEE) Uppsala, Sweden, Oct. 2-6, 2006. pp. 894-897.

Chapter 21. Lou et al., "Acoustic Wave Based Microfluidics and Lab-on-a-Chip," in *Modeling and Measurement Methods for Acoustic Waves and for Acoustic Microdevices*. InTech: Aug. 28, 2013. 515-56.

Chen et al., "Characteristics of Dual Mode AlN Thin Film Bulk Acoustic Wave Resonators," May 19-21, 2008, *IEEE International Frequency Control Symposium*, pp. 609-614.

Fan et al., "An adaptive feedback circuit for MEMS resonators," Mar. 1, 2011, *Journal of Micromechanics and Microengineering*, vol. 21; 10 pages.

Fu et al., "Aluminium Nitride thin Film Acoustic Wave Device for Microfluidic and Biosensing Applications," Sep. 1, 2010, *Acoustic Waves*, retrieved on Nov. 14, 2016 from the Internet. Retrieved from the Internet: <URL:https://www/researchgate/net/profile/MPY_Desmulliez/publication/267951195_Aluminium_Nitride_thin_Film-Acoustin_Wave_Device_for_Microfluidic_and_Biosensing_Applications/links/5450dd8b0cf295b561637e62.pdf>; 263-98pgs.

International Patent Application No. PCT/US2016/059312, filed Oct. 28, 2016; International Search Report / Written Opinion dated Feb. 13, 2017; 12 pages.

International Patent Application No. PCT/US2016/059312, filed Oct. 28, 2016; International Preliminary Report on Patentability dated May 11, 2018; 8 pages.

International Patent Application No. PCT/US2016/059327, filed Oct. 28, 2016; International Search Report / Written Opinion dated Feb. 13, 2017; 15 pages.

International Patent Application No. PCT/US2016/059327, filed Oct. 28, 2016; International Preliminary Report on Patentability dated May 11, 2018; 9 pages.

International Patent Application No. PCT/US2016/059677, filed Oct. 31, 2016; International Search Report / Written Opinion dated May 18, 2017; 11 pages.

International Patent Application No. PCT/US2016/059677, filed Oct. 31, 2016; International Preliminary Report on Patentability dated May 24, 2018; 9 pages.

Katardjiev et al., "Recent developments in thin film electro-acoustic technology for biosensor applications," Oct. 19, 2011, *Vacuum*, 86(5):520-31.

"The Laser MicroJet® Technology: A Simple Principle," Synova: Cool Last Micro-Machining, Feb. 17, 2015; 8 pages.

Luo, et al., Chapter 21, "Acoustic Wave Based Microfluidics and Lab-on-a-Chip," *Modeling and Measurement Methods for Acoustic Waves and for Acoustic Microdevices*, InTech, Aug. 28, 2013, pp. 515-556.

(56) References Cited

OTHER PUBLICATIONS

Miller, "The Stokes-Einstein Law for Diffusion in Solution," *Proceedings of the Royal Society of London. Series A, Containing Papers of a Mathematical and Physical Character* (1905-1934), Jan. 1924, 106(70):724-49.
Montagut, Yeison et al. "QCM Technology in Biosensors," Biosensors—Emerging Materials and Applications, Chapter 9, 2011, INTECH Open Access Publisher, pp. 153-178.
Nguyen et al., "Micromixers—a review," Dec. 8, 2004, *Journal of Micromechanics and Microengineering*, vol. 15: pp. R1-R16.
Qin et al., "Analytical Study of Dual-Mode Thin Film Bulk Acoustic Resonators (FBARs) Based on ZnO and AlN Films with Tilted C-Axis Orientation," Aug. 2010, *IEEE Transactions on Ultrasonics, Ferroelectrics, and Frequency Control*, 57(8):1840-53.
Rabus et al., "A high sensitivity open loop electronics for gravimetric acoustic wave-based sensors," Jun. 2013, *IEEE Transactions on Ultrasonics, Ferroelectrics, and Frequency Control*, 60(6):1219-1226.
Ramakrishnan, et al., "Resonant Frequency Characteristics of a SAW Device Attached to Resonating Micropillars," 2012, *Sensors*, 12(4):3789-97.
Stroock et al., "Chaotic Mixer for Microchannels," Jan. 25, 2002, *Science*, vol. 295: pp. 647-651.
Suh et al., "A Review on Mixing in Microfluidics," Sep. 30, 2010, *Micromachines*, 1(3):82-111.
Through Silicon Vias (TSV) for backside electrical connection are common in devices https://en.wikipedia.org/wiki/Through-silicon_via.
Voiculescu et al., "Acoustic wave based MEMS devices for biosensing applications," Dec. 21, 2011, *Biosensors and Bioelectronics*, 33(1):1-9.
Wingqvist et al., "Shear mode AlN thin film electro-acoustic resonant sensor operation in viscous media," Mar. 30, 2007, *International Journal Devoted to Research and Development of Physical and Chemical Transducers: Sensors and Actuator B Chemical*, 123(1):466-73.
Zhang et al., "A Microfluidic Love-Wave Biosensing Device for PSA Detection Based on an Aptamer Beacon Probe," 2015, *Sensors*, 15:13839-850.
Zhang et al., "A single-chip biosensing platform integrating FBAR sensor with digital microfluidic device," IEEE International Ultrasonics Symposium Proceedings, (IEEE) Tianjin, China, Sep. 3, 2014. pp. 1521-1523.
Xu et al., "In-Liquid Quality Factor Improvement for Film Bulk Acoustic Resonators by Integration of Microfluidic Channels," Jun. 2009, *IEEE Electronic Device Letters*, 30(6): 647-49.

\* cited by examiner

FLUIDIC DEVICE INCLUDING BAW RESONATORS ALONG OPPOSING CHANNEL SURFACES

STATEMENT OF RELATED APPLICATIONS

This application is a non-provisional of U.S. provisional patent application Ser. No. 62/248,392, filed Oct. 30, 2015, the disclosure of which is hereby incorporated herein by reference in its entirety. Subject matter disclosed herein also relates to U.S. patent application Ser. No. 15/337,338 entitled "Sensor Device with BAW Resonator and Through-Substrate Fluidic Vias" filed or to be filed on Oct. 28, 2016, the contents of which are hereby incorporated by reference as if set forth fully herein.

TECHNICAL FIELD

The present disclosure relates to fluidic devices incorporating acoustic resonators, including fluidic devices suitable for biosensing or biochemical sensing applications.

BACKGROUND

A biosensor (or biological sensor) is an analytical device including a biological element and a transducer that converts a biological response into an electrical signal. Certain biosensors involve a selective biochemical reaction between a specific binding material (e.g., an antibody, a receptor, a ligand, etc.) and a target species (e.g., molecule, protein, DNA, virus, bacteria, etc.), and the product of this highly specific reaction is converted into a measurable quantity by a transducer. Other sensors may utilize a non-specific binding material capable of binding multiple types or classes of molecules or other moieties that may be present in a sample, such as may be useful in chemical sensing applications. The term "functionalization material" may be used herein to generally relate to both specific and non-specific binding materials. Transduction methods used with biosensors may be based on various principles, such as electrochemical, optical, electrical, acoustic, and so on. Among these, acoustic transduction offers a number of potential advantages, such as being real time, label-free, and low cost, as well as exhibiting high sensitivity.

An acoustic wave device employs an acoustic wave that propagates through or on the surface of a piezoelectric material, whereby any changes to the characteristics of the propagation path affect the velocity and/or amplitude of the wave. Presence of functionalization material embodied in a specific binding material along an active region of an acoustic wave device permits a specific analyte to be bound to the functionalization material, thereby altering the mass being vibrated by the acoustic wave and altering the wave propagation characteristics (e.g., velocity, thereby altering resonance frequency). Changes in velocity can be monitored by measuring the frequency, amplitude magnitude, or phase characteristics of the sensor and can be correlated to a physical quantity being measured.

In the case of a piezoelectric crystal resonator, an acoustic wave may embody a bulk acoustic wave (BAW) propagating through the interior (or "bulk") of a substrate, or a surface acoustic wave (SAW) propagating on the surface of the substrate. SAW devices involve transduction of acoustic waves (commonly including two-dimensional Rayleigh waves) utilizing interdigital transducers along the surface of a piezoelectric material, with the waves being confined to a penetration depth of about one wavelength. In a BAW device, three wave modes can propagate, namely, one longitudinal mode (embodying longitudinal waves, also called compressional/extensional waves, and two shear modes (embodying shear waves, also called transverse waves), with longitudinal and shear modes respectively identifying vibrations where particle motion is parallel to or perpendicular to the direction of wave propagation. The longitudinal mode is characterized by compression and elongation in the direction of the propagation, whereas the shear modes consist of motion perpendicular to the direction of propagation with no local change of volume. Longitudinal and shear modes propagate at different velocities. In practice, these modes are not necessarily pure modes as the particle vibration, or polarization, is neither purely parallel nor purely perpendicular to the propagation direction. The propagation characteristics of the respective modes depend on the material properties and propagation direction respective to the crystal axis orientations. Since shear waves exhibit a very low penetration depth into a liquid, a device with pure or predominant shear modes can operate in liquids without significant radiation losses (in contrast with longitudinal waves, which can be radiated in liquid and exhibit significant propagation losses). The ability to create shear displacements is beneficial for operation of acoustic wave devices with fluids (e.g., liquids) because shear waves do not impart significant energy into fluids.

Certain piezoelectric thin films are capable of exciting both longitudinal and shear mode resonance, such as hexagonal crystal structure piezoelectric materials including (but not limited to) aluminum nitride (AlN) and zinc oxide (ZnO). To excite a wave including a shear mode using a piezoelectric material arranged between electrodes, a polarization axis in a piezoelectric thin film must generally be non-perpendicular to (e.g., tilted relative to) the film plane. In biological sensing applications involving liquid media, the shear component of the resonator is used. In such applications, piezoelectric material may be grown with a c-axis orientation distribution that is non-perpendicular relative to a face of an underlying substrate to enable a BAW resonator structure to exhibit a dominant shear response upon application of an alternating current signal across electrodes thereof. Conversely, a piezoelectric material grown with a c-axis orientation that is perpendicular relative to a face of an underlying substrate will exhibit a dominant longitudinal response upon application of an alternating current signal across electrodes thereof.

Typically, BAW devices are fabricated by micro-electro-mechanical systems (MEMS) fabrication techniques, owing to the need to provide microscale features suitable for facilitating high-frequency operation. In the context of biosensors, functionalization materials (e.g., specific binding materials; also known as bioactive probes or agents) may be deposited on sensor surfaces by microarray spotting (also known as microarray printing) using a microarray spotting needle. Functionalization materials providing non-specific binding utility (e.g., permitting binding of multiple types or species of molecules) may also be used in certain contexts, such as chemical sensing.

Biochemical sensors may incorporate multiple resonators, such as at least one reference region devoid of functionalization material, as well as one or more sensing regions including one or more functionalization materials. It may be desirable to incorporate multiple sensing regions in series or parallel configurations. Presence of multiple resonators (as well as fluidic connections) presents packaging constraints that tend to increase the size and cost of sensor devices, due to the need to provide multiple electrical and fluidic connections. Additionally, conventional biochemical sensing devices may suffer from inconsistent distribution of target species in a sample and/or a low rate of analyte binding that may extend the time necessary to complete measurement of a particular sample.

Accordingly, there is a need for fluidic devices incorporating multiple BAW resonator structures, such as for biosensing or biochemical sensing applications, and that overcome limitations associated with conventional devices.

SUMMARY

The present disclosure relates to the use of multiple bulk acoustic wave (BAW) resonator structures arranged along opposing surfaces of a channel arranged to receive a fluid. The use of BAW resonator structures arranged along opposing surfaces of a channel may provide various technical benefits in certain embodiments, including reducing the footprint of a multi-resonator fluidic device; increasing a rate of analyte binding and thereby reducing the time necessary to complete a desired measurement of a sample; and/or enhancing mixing of constituents of a sample and thereby increasing uniformity of analyte distribution.

In one aspect of the present disclosure, a fluidic device comprises a channel arranged to receive a fluid; a first BAW resonator structure arranged between a first substrate and a first surface bounding the channel; and a second BAW resonator structure arranged between a second substrate and a second surface bounding the channel, wherein the second surface opposes the first surface. The first BAW resonator structure includes a first piezoelectric material, a first distal electrode arranged between the first piezoelectric material and the first substrate, and a first proximal electrode arranged between the first piezoelectric material and the channel, wherein at least a portion of the first piezoelectric material is arranged between the first distal electrode and the first proximal electrode to form a first active region; and the second BAW resonator structure includes a second piezoelectric material, a second distal electrode arranged between the second piezoelectric material and the second substrate, and a second proximal electrode arranged between the second piezoelectric material and the channel, wherein at least a portion of the second piezoelectric material is arranged between the second distal electrode and the second proximal electrode to form a second active region. In certain embodiments, one or both of first and second active regions may be overlaid with at least one functionalization material to enable the corresponding BAW resonator structure to provide biochemical sensing utility.

In certain embodiments, the fluidic device includes at least one intermediate layer defining at least a portion of the channel, wherein the at least one intermediate layer is arranged between the first BAW resonator structure and the second BAW resonator structure.

In certain embodiments, the first piezoelectric material comprises a c-axis having an orientation distribution that is predominantly non-parallel to normal of a face of the first substrate; and/or the second piezoelectric material comprises a c-axis having an orientation distribution that is predominantly non-parallel to normal of a face of the second substrate. Under appropriate conditions, presence of a c-axis having an orientation distribution that is predominantly non-parallel to normal of a face of a substrate enables a BAW resonator structure to be configured to exhibit a dominant shear response upon application of an alternating current signal across a distal electrode and a proximal electrode thereof (e.g., as may be desirable in the context of a BAW resonator structure providing sensing utility).

In certain embodiments, the first piezoelectric material comprises a c-axis having an orientation distribution that is predominantly non-parallel to normal of the face of the first substrate, and the first BAW resonator structure is configured to exhibit a dominant shear response upon application of an alternating current signal across the first distal electrode and the first proximal electrode; and the second piezoelectric material comprises a c-axis having an orientation distribution that is predominantly non-parallel to normal of the face of the second substrate, and the second BAW resonator structure is configured to exhibit a dominant shear response upon application of an alternating current signal across the second distal electrode and the second proximal electrode. Such an embodiment may include both BAW resonator structures providing sensing utility.

In certain embodiments, the first BAW resonator structure is configured to exhibit a dominant longitudinal response upon application of an alternating current signal across the first distal electrode and the first proximal electrode; and the second piezoelectric material comprises a c-axis having an orientation distribution that is predominantly non-parallel to normal of the face of the second substrate, and the second BAW resonator structure is configured to exhibit a dominant shear response upon application of an alternating current signal across the second distal electrode and the second proximal electrode. Such an embodiment may include the first BAW resonator structure providing sensing utility, and the second BAW resonator structure providing agitation or mixing utility.

In certain embodiments, at least one of the first BAW resonator structure or the second BAW resonator structure includes a solidly mounted resonator (SMR) structure. For example, in certain embodiments, the first BAW resonator structure comprises a first acoustic reflector structure arranged between the first substrate and the first distal electrode, and the second BAW resonator structure comprises a second acoustic reflector structure arranged between the second substrate and the second distal electrode.

In certain embodiments, at least one of the first BAW resonator structure or the second BAW resonator structure includes a film bulk acoustic wave resonator (FBAR) structure in which a cavity is provided instead of an acoustic reflector to reduce or prevent dissipation of acoustic energy in a substrate. For example, in certain embodiments, the first substrate defines a first recess, and a first support layer is arranged between the first recess and the first BAW resonator structure; and the second substrate defines a second recess, and a second support layer is arranged between the second recess and the second BAW resonator structure. In certain embodiments, the first and second support layers may be removed or omitted. In certain embodiments the first substrate defines a first recess proximate to the first bulk acoustic wave resonator structure, and the second substrate defines a second recess proximate to the second bulk acoustic wave resonator structure.

In certain embodiments, the first active region is arranged at a first location along the first surface disposed a first distance from an upstream end of the channel, and the second active region is arranged at a second location along the second surface disposed the first distance from the upstream end of the channel. In certain embodiments, the first and second active regions may be substantially registered (e.g., vertically aligned) with one another along opposing surfaces of the channel.

In certain embodiments, the first active region is arranged at a first location along the first surface disposed a first distance from an upstream end of the channel, and the second active region is arranged at a second location along the second surface disposed a second distance from the upstream end of the channel, wherein the second distance is greater than the first distance.

In certain embodiments, at least one functionalization material arranged over at least a portion of at least one of the first active region or the second active region, wherein the at least one functionalization material is in fluid communication with the channel. In certain embodiments, the at least one functionalization material comprises a specific binding material; in other embodiments, the at least one functionalization material comprises a non-specific binding material. In certain embodiments, different active regions are overlaid with binding materials that differ in composition or binding type. In certain embodiments, one-dimensional or two-dimensional arrays of active regions of MEMS resonator structures with associated functionalization materials may be arranged over and/or under one or more channels of a fluidic device.

In certain embodiments, at least one first functionalization material is arranged over at least a portion of the first active region, wherein the at least one first functionalization material is in fluid communication with the channel, and a first self-assembled monolayer is arranged between the at least one first functionalization material and the first proximal electrode; and/or at least one second functionalization material is arranged over at least a portion of the second active region, wherein the at least one second functionalization material is in fluid communication with the channel, and a second self-assembled monolayer is arranged between the at least one second functionalization material and the second proximal electrode.

In certain embodiments, at least one first functionalization material is arranged over at least a portion of the first active region, wherein the at least one first functionalization material is in fluid communication with the channel, a first self-assembled monolayer is arranged between the at least one first functionalization material and the first proximal electrode, a first interface layer is arranged between the first self-assembled monolayer and the first proximal electrode, and a first hermeticity layer is arranged between the first interface layer and the first proximal electrode; and/or at least one second functionalization material is arranged over at least a portion of the second active region, wherein the at least one second functionalization material is in fluid communication with the channel, a second self-assembled monolayer is arranged between the at least one second functionalization material and the second proximal electrode, a second interface layer is arranged between the second self-assembled monolayer and the second proximal electrode, and a second hermeticity layer is arranged between the second interface layer and the second proximal electrode.

In certain embodiments, a plurality of first bulk acoustic wave resonator structures is arranged between the first substrate and the first surface bounding the channel; and/or a plurality of second bulk acoustic wave resonator structures is arranged between the second substrate and the second surface bounding the channel.

In another aspect of the disclosure, a method for biological or chemical sensing comprises: (i) supplying a fluid containing a target species into the channel of a fluidic device as disclosed herein in which the first BAW resonator structure is configured to exhibit a dominant shear response upon application of an alternating current signal across the first distal electrode and the first proximal electrode, and the second BAW resonator structure is configured to exhibit a dominant shear response upon application of an alternating current signal across the second distal electrode and the second proximal electrode, wherein said supplying is configured to cause at least some of the target species to bind to at least one first functionalization material arranged over the first active region, and to cause at least some of the target species to bind to at least one second functionalization material arranged over the second active region; (ii) inducing a first bulk acoustic wave in the first active region, and sensing a change in at least one of a frequency property, an amplitude magnitude property, or a phase property of the first BAW resonator structure to indicate at least one of presence or quantity of target species bound to the at least one first functionalization material; and (iii) inducing a second bulk acoustic wave in the second active region, and sensing a change in at least one of a frequency property, an amplitude magnitude property, or a phase property of the second BAW resonator structure to indicate at least one of presence or quantity of target species bound to the at least one second functionalization material.

In another aspect of the disclosure, a method for biological or chemical sensing comprises: (i) supplying a fluid containing a target species into the channel of a fluidic device disclosed herein in which the first BAW resonator structure is configured to exhibit a dominant longitudinal response upon application of an alternating current signal across the first distal electrode and the first proximal electrode and the second BAW resonator structure is configured to exhibit a dominant shear response upon application of an alternating current signal across the second distal electrode and the second proximal electrode, wherein said supplying is configured to cause at least some of the target species to bind to at least one functionalization material arranged over the second active region; (ii) inducing a first bulk acoustic wave in the first active region to promote at least one of mixing of the fluid or movement of the target species; and (iii) inducing a second bulk acoustic wave in the second active region, and sensing a change in at least one of a frequency property, an amplitude magnitude property, or a phase property of the second bulk acoustic wave resonator structure to indicate at least one of presence or quantity of target species bound to the at least one functionalization material.

In another aspect of the present disclosure, a method for fabricating a fluidic device comprises: fabricating a first bulk acoustic wave resonator structure; fabricating a second bulk acoustic wave resonator structure; and arranging at least one intermediate layer defining lateral boundaries of a channel arranged to receive a fluid between the first BAW resonator structure and the second BAW resonator structure; wherein the first BAW resonator structure is arranged proximate to a first surface bounding the channel, the second BAW resonator structure is arranged proximate to a second surface bounding the channel, and the second surface opposes the first surface.

In certain embodiments, (i) the first BAW resonator structure is arranged between a first substrate and the first surface bounding the channel, wherein the first BAW resonator structure includes a first piezoelectric material, a first distal electrode arranged between the first piezoelectric material and the first substrate, and a first proximal electrode arranged between the first piezoelectric material and the channel, wherein at least a portion of the first piezoelectric material is arranged between the first distal electrode and the first proximal electrode to form a first active region; (ii) the second BAW resonator structure is arranged between a second substrate and a second surface bounding the second channel, wherein the second BAW resonator structure includes a second piezoelectric material, a second distal electrode arranged between the second piezoelectric material and the second substrate, and a second proximal electrode arranged between the second piezoelectric material and the channel, wherein at least a portion of the second piezoelectric material is arranged between the second distal electrode and the second proximal electrode to form a second active region; and (iii) the method further comprises applying at least one functionalization material over at least a portion of at least one of the first active region or the second active region, wherein the at least one functionalization material is in fluid communication with the channel.

In certain embodiments, the method further comprises forming at least one self-assembled monolayer over at least a portion of the first active region or the second active region, wherein the at least one functionalization material is applied over the at least one self-assembled monolayer. In certain embodiments, the method further comprises forming at least one interface layer over at least a portion of the first active region or the second active region, wherein the at least one self-assembled monolayer is formed over the at least one interface layer.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure and, together with the description, serve to explain the principles of the disclosure.

DETAILED DESCRIPTION

Figure 1:
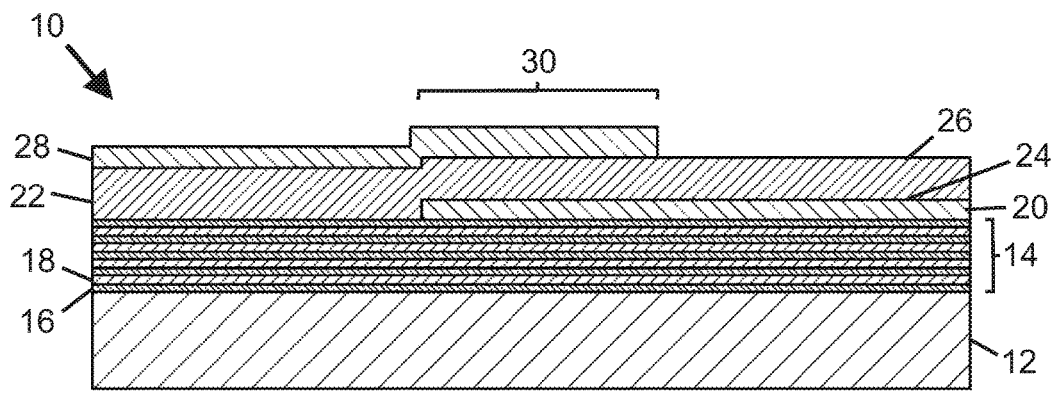
FIG. 1 is a schematic cross-sectional view of a portion of a bulk acoustic wave (BAW) resonator device usable with embodiments disclosed herein, including an active region with a piezoelectric material between overlapping portions of a top side electrode and a bottom side electrode.

Embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the scope of the present disclosure. As used herein, the term "and/or" includes any and all combinations of one or more of the associated listed items.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

The present disclosure relates to the use of multiple bulk acoustic wave (BAW) resonator structures arranged along opposing surfaces of a channel arranged to receive a fluid. The use of BAW resonator structures arranged along opposing surfaces of a channel may provide various technical benefits, such as reducing the footprint of a multi-resonator fluidic device with a given number of multiple active regions; increasing a rate of analyte binding, thereby reducing the time necessary to complete a desired measurement of a sample; and/or enhancing mixing of constituents of a sample, thereby increasing uniformity of analyte distribution. In certain embodiments, multiple active regions including the same or different functionalization materials may be configured in one-dimensional or two-dimensional arrays and arranged in fluid communication with one or more channels of a fluidic device.

In one aspect of the present disclosure, a fluidic device comprises a channel arranged to receive a fluid; a first BAW resonator structure arranged between a first substrate and a first surface bounding the channel; and a second BAW resonator structure arranged between a second substrate and a second surface bounding the channel, wherein the second surface opposes the first surface. The first BAW resonator structure includes a first piezoelectric material, a first distal electrode arranged between the first piezoelectric material and the first substrate, and a first proximal electrode arranged between the first piezoelectric material and the channel, wherein at least a portion of the first piezoelectric material is arranged between the first distal electrode and the first proximal electrode to form a first active region; and the second BAW resonator structure includes a second piezoelectric material, a second distal electrode arranged between the second piezoelectric material and the second substrate, and a second proximal electrode arranged between the second piezoelectric material and the channel, wherein at least a portion of the second piezoelectric material is arranged between the second distal electrode and the second proximal electrode to form a second active region. In certain embodiments, one or both of first and second active regions may be overlaid with at least one functionalization material to enable the corresponding BAW resonator structure to provide biochemical sensing utility.

Under typical operating conditions, flows in microfluidic channels (also termed "microchannels") are laminar. Fluids in laminar flow tend to follow parallel streamline paths, such that the chaotic fluctuations of velocity that tend to homogenize fluids in turbulent flows are absent. Multiple fluids introduced in a standard microchannel generally will not mix with each other, except at a common interface between the fluids via diffusion, and the diffusion process is typically slow compared with the flow of fluid along a principal axis of a microfluidic channel. The same principles that inhibit rapid mixing of fluids flowing under laminar conditions in a microfluidic channel also affect the distribution of analytes contained in one or more fluids flowing within a microfluidic channel. Fick's first law of diffusion states that flux moves from regions of high concentration to regions of low concentration. Secondarily, the flux rate is proportional to the concentration gradient difference. Consider a volume of fluid containing an analyte and advancing in a horizontal direction through a microfluidic channel having functionalization material arranged along a bottom surface of the channel, where the fluid volume may be modeled as a moving "stack" of horizontal fluid layers. Even if it is assumed that analyte concentration is constant in each layer of the stack forming the fluid volume upon entering the microfluidic channel, following passage of the fluid volume over the functionalization material, a lowermost fluid layer of the stack will exhibit reduced or depleted analyte concentration due to binding of analyte with the functionalization material. But since diffusion is slow in a direction perpendicular to the direction of fluid flow through the microfluidic channel, and analyte needs to diffuse to a surface bearing functionalization material to bind, analyte present in fluid layers other than the lowermost fluid layer may not be available for binding with the functionalization material along the bottom surface of the channel within a reasonable period of time. Analyte concentration may remain stratified within the channel until diffusion occurs. Additionally, large analyte molecules may require a long time to bind with functionalization material. Due to these considerations, analyte binding rate is limited, and an extended time may be necessary to complete a desired measurement of a sample.

In certain embodiments of the present disclosure, multiple BAW resonator structures are arranged along opposing surfaces of a channel, wherein each BAW resonator structure is configured to exhibit a dominant shear response upon application of an alternating current signal across electrodes thereof, and the active region of each BAW resonator structure is overlaid with at least one functionalization material. For example, active regions with functionalization material may be arranged along top and bottom surfaces of a microfluidic channel, thereby permitting analyte present in a lowermost fluid layer to bind with functionalization material along the bottom surface of the channel, and permitting analyte present in an uppermost fluid layer to bind with functionalization material along the top surface of the channel. Such a configuration may significantly increase analyte binding rate (despite a limited rate of analyte diffusion in a vertical direction within the microfluidic channel) and thereby reduce a length of time necessary to complete a desired measurement of a sample.

In certain embodiments of the present disclosure, multiple BAW resonator structures are arranged along opposing surfaces of a channel, wherein a first BAW resonator structure is configured to exhibit a dominant shear response upon application of an alternating current across electrodes thereof and includes an active region overlaid with at least one functionalization material to permit binding of an analyte, and a second BAW resonator structure opposing the first BAW resonator structure is configured to exhibit a dominant longitudinal response upon application of an alternating current across electrodes thereof and includes an active region without functionalization material, with the second BAW resonator structure being configured to impart acoustic energy into the fluid to enhance agitation or mixing. The presence of the second BAW resonator structure may reduce stratification of analyte concentration and/or enhance analyte transport to an active region within a microfluidic channel of a biosensor device, thereby reducing a length of time necessary to complete a desired measurement of a sample.

In certain embodiments of the present disclosure, multiple BAW resonator structures are arranged along opposing surfaces of a channel, wherein a first BAW resonator structure is configured to exhibit a dominant shear response upon application of an alternating current across electrodes thereof and includes an active region overlaid with at least one functionalization material to permit binding of an analyte, a second BAW resonator structure arranged upstream of the first BAW resonator structure is configured to exhibit a dominant longitudinal response upon application of an alternating current across electrodes thereof and includes an active region without functionalization material and is configured to impart acoustic energy into the fluid to enhance agitation or mixing, and at least one additional BAW resonator structure is arranged on a surface opposing one or more of the first BAW resonator structure and/or the second BAW resonator structure. Presence of the second BAW resonator structure may reduce stratification of analyte concentration and/or enhance analyte transport to an active region within a microfluidic channel of a biosensor device, thereby reducing a length of time necessary to complete a desired measurement of a sample.

FIG. 1 is a schematic cross-sectional view of a portion of a bulk acoustic wave MEMS resonator device 10 useable with embodiments disclosed herein. The bulk acoustic wave MEMS resonator device 10 includes a substrate 12 (e.g., typically silicon or another semiconductor material), an acoustic reflector 14 arranged over the substrate 12, a piezoelectric material 22, and bottom and top side electrodes 20, 28. The bottom side electrode 20 is arranged along a portion of a lower surface 24 of the piezoelectric material 22 (between the acoustic reflector 14 and the piezoelectric material 22), and the top side electrode 28 is arranged along a portion of an upper surface 26 of the piezoelectric material 22. An area in which the piezoelectric material 22 is arranged between overlapping portions of the top side electrode 28 and the bottom side electrode 20 is considered an active region 30 of the resonator device 10. The acoustic reflector 14 serves to reflect acoustic waves and therefore reduce or avoid their dissipation in the substrate 12. In certain embodiments, the acoustic reflector 14 includes alternating thin layers 16, 18 of different materials (e.g., silicon oxicarbide [SiOC], silicon nitride [$Si_3N_4$], silicon dioxide [$SiO_2$], aluminum nitride [AlN], tungsten [W], and molybdenum [Mo]), optionally embodied in a quarter-wave Bragg mirror, deposited over the substrate 12. In certain embodiments, other types of acoustic reflectors may be used. Steps for forming the resonator device 10 may include depositing the acoustic reflector 14 over the substrate 12, followed by deposition of the bottom side electrode 20, followed by growth (e.g., via sputtering or other appropriate methods) of the piezoelectric material 22, followed by deposition of the top side electrode 28.

Depending on the c-axis orientation distribution of the piezoelectric material 22 and an input signal, a BAW resonator device may exhibit a dominant shear response (e.g., if the c-axis orientation distribution is non-perpendicular relative to a face of an underlying substrate) or a dominant longitudinal response (e.g., including cases in which the c-axis orientation distribution is non-perpendicular relative to a face of an underlying substrate).

The bulk acoustic wave MEMS resonator device 10 shown in FIG. 1 lacks any layers (e.g., including functionalization material) overlying the active region 30 that would permit the device 10 to be used as a biochemical sensor. If desired, at least portions of the bulk acoustic wave MEMS resonator device 10 shown in FIG. 1 (e.g., including the active region 30) may be overlaid with various layers, such as a hermeticity layer (e.g., to protect the top side electrode 28 from corrosion in a liquid environment), an interface layer (e.g., to enable attachment of a functionalization material), and functionalization material, which may include specific binding material or non-specific binding material. In certain embodiments, a self-assembled monolayer (SAM) may be deposited prior to the functionalization material to facilitate attachment of the functionalization material.

Figure 2:
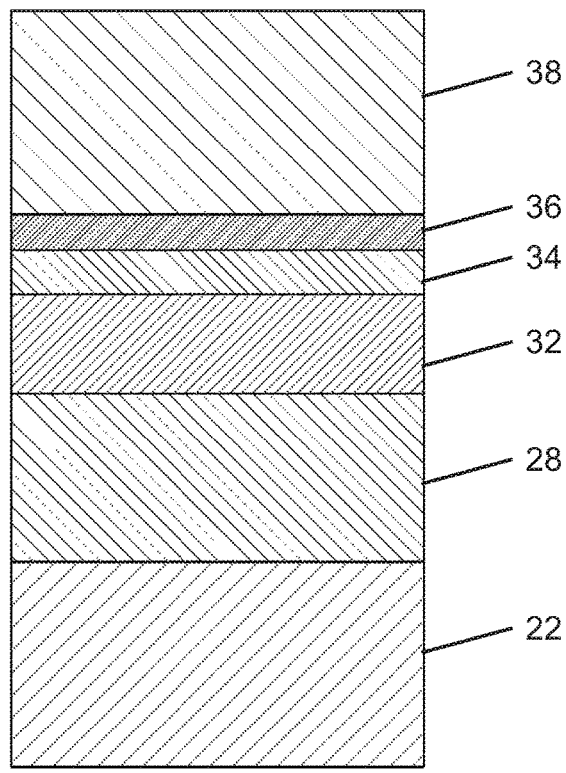
FIG. 2 is a schematic cross-sectional view of an upper portion of a BAW resonator device including a piezoelectric material and a top side electrode overlaid with a hermeticity layer, an interface layer, a self-assembled monolayer, and a functionalization (e.g., specific binding) material.

FIG. 2 is a schematic cross-sectional view of an upper portion of a bulk acoustic wave resonator device including a piezoelectric material 22 and a top side electrode 28 overlaid with a hermeticity layer 32, an interface layer 34, a self-assembled monolayer (SAM) 36, and functionalization (e.g., specific binding) material 38. In certain embodiments, one or more blocking materials may be applied during fabrication, such as over portions of an interface layer to prevent localized attachment of one or more subsequently deposited layers, or (if applied over selected regions of a SAM or a functionalization material) to prevent analyte capture in regions not overlying an active region of the BAW resonator device.

In certain embodiments, photolithography may be used to promote patterning of interface material or blocking material over portions of a MEMS resonator device. Photolithography involves use of light to transfer a geometric pattern from a photomask to a light-sensitive chemical photoresist on a substrate and is a process well known to those of ordinary skill in the semiconductor fabrication art. Typical steps employed in photolithography include wafer cleaning, photoresist application (involving either positive or negative photoresist), mask alignment, and exposure and development. After features are defined in photoresist on a desired surface, an interface layer may be patterned by etching in one or more gaps in a photoresist layer, and the photoresist layer may be subsequently removed (e.g., using a liquid photoresist stripper, by ashing via application of an oxygen-containing plasma, or another removal process).

In certain embodiments, an interface layer (e.g., arrangeable between a top side electrode and a SAM) includes a hydroxylated oxide surface suitable for formation of an organosilane SAM. A preferred interface layer material including a hydroxylated oxide surface is silicon dioxide [$SiO_2$]. Alternative materials incorporating hydroxylated oxide surfaces for forming interface layers include titanium dioxide [$TiO_2$], tantalum pentoxide [$Ta_2O_5$], hafnium oxide [$HfO_2$], or aluminum oxide [$Al_2O_3$]. Other alternative materials incorporating hydroxylated oxide surfaces will be known to those skilled in the art, and these alternatives are considered to be within the scope of the present disclosure.

In other embodiments, an interface layer (e.g., arrangeable between a top side electrode and a SAM), or at least one electrode that is devoid of an overlying interface layer, includes gold or another noble metal (e.g., ruthenium, rhodium, palladium, osmium, iridium, platinum, or silver) suitable for receiving a thiol-based SAM that may be overlaid with functionalization material.

In certain embodiments incorporating electrode materials subject to corrosion, a hermeticity layer may be applied between a top side electrode and an interface layer. A hermeticity layer may be unnecessary when noble metals (e.g., gold, platinum, etc.) are used for top side electrodes. If provided, a hermeticity layer preferably includes a dielectric material with a low water vapor transmission rate (e.g., no greater than 0.1 $g/m^2/day$). Following deposition of a hermeticity layer and an interface layer, a SAM may be formed over the interface layer, with the SAM including an organosilane material in certain embodiments. The hermeticity layer protects a reactive electrode material (e.g., aluminum or aluminum alloy) from attack in corrosive liquid environments, and the interface layer facilitates proper chemical binding of the SAM.

In certain embodiments, a hermeticity layer and/or an interface layer may be applied via one or more deposition processes such as atomic layer deposition (ALD), chemical vapor deposition (CVD), or physical vapor deposition (PVD). Of the foregoing processes, ALD is preferred for deposition of at least the hermeticity layer (and may also be preferable for deposition of the interface layer) due to its ability to provide excellent conformal coating with good step coverage over device features so as to provide layer structures that are free of pinholes. Moreover, ALD is capable of forming uniformly thin layers that provide relatively little damping of acoustic vibrations that would otherwise result in degraded device performance. Adequacy of coverage is important for a hermeticity layer (if present) to avoid corrosion of the underlying electrode. If ALD is used for deposition of a hermeticity layer, then in certain embodiments a hermeticity layer may include a thickness in a range of from about 10 nm to about 25 nm. In certain embodiments, hermeticity layer thickness is about 15 nm, or from about 12 nm to about 18 nm. Conversely, if another process such as chemical vapor deposition is used, then a hermeticity layer may include a thickness in a range of from about 80 nm to about 150 nm or more, or in a range of from about 80 nm to about 120 nm. Considering both of the foregoing processes, hermeticity layer thicknesses may range from about 5 nm to about 150 nm. If ALD is used for deposition of an interface layer, then an interface layer may include a thickness in a range of from about 5 nm to about 15 nm. In certain embodiments, an interface layer may include a thickness of about 10 nm, or in a range of from about 8 nm to about 12 nm. Other interface layer thickness ranges and/or deposition techniques other than ALD may be used in certain embodiments. In certain embodiments, a hermeticity layer and an interface layer may be sequentially applied in a vacuum environment, thereby promoting a high-quality interface between the two layers.

If provided, a hermeticity layer may include an oxide, a nitride, or an oxynitride material serving as a dielectric material and having a low water vapor transmission rate (e.g., no greater than 0.1 $g/m^2/day$) according to certain embodiments. In certain embodiments, a hermeticity layer includes at least one of aluminum oxide ($Al_2O_3$) or silicon nitride (SiN). In certain embodiments, an interface layer includes at least one of $SiO_2$, $TiO_2$, or $Ta_2O_5$. In certain embodiments, multiple materials may be combined in a single hermeticity layer, and/or a hermeticity layer may include multiple sublayers of different materials. Preferably, a hermeticity layer is further selected to promote compatibility with an underlying reactive metal (e.g., aluminum or aluminum alloy) electrode structure of an acoustic resonator structure. Although aluminum or aluminum alloys are frequently used as electrode materials in BAW resonator structures, various transition and post-transition metals can be used for such electrodes.

Following deposition of an interface layer (optionally arranged over an underlying hermeticity layer), a SAM is preferably formed over the interface layer. SAMs are typically formed by exposure of a solid surface to amphiphilic molecules with chemical groups that exhibit strong affinities for the solid surface. When an interface layer comprising a hydroxylated oxide surface is used, then organosilane SAMs are particularly preferred for attachment to the hydroxylated oxide surface. Organosilane SAMs promote surface bonding through silicon-oxygen (Si—O) bonds. More specifically, organosilane molecules include a hydrolytically sensitive group and an organic group and are therefore useful for coupling inorganic materials to organic polymers. An organosilane SAM may be formed by exposing a hydroxylated surface to an organosilane material in the presence of trace amounts of water to form intermediate silanol groups. These groups then react with free hydroxyl groups on the hydroxylated surface to covalently immobilize the organosilane. Examples of possible organosilane-based SAMs that are compatible with interface layers incorporating hydroxylated oxide surfaces include 3-glycidoxypropyltrimethoxysilane (GPTMS), 3-mercaptopropyltrimethoxysilane (MPTMS), 3-aminopropyltrimethoxysilane (APTMS), and octadecyltrimethoxysilane (OTMS), including their ethoxy- and chloro-variants. Additional silanes that may be used for SAMs include poly(ethylene glycol) (PEG) conjugated variants. Those skilled in the art will recognize that other alternatives exist, and these alternatives are considered to be within the scope of the present disclosure. An exemplary SAM may include a thickness in a range of at least 0.5 nm or more. Preferably, a SAM readily binds to the locally patterned interface layer but does not readily bind to other adjacent material layers (e.g., a hermeticity layer, a piezoelectric material, and/or a blocking material layer).

When an electrode(s) and/or interface layer comprising gold or another noble metal is used, then thiol-based (e.g., alkanethiol-based) SAMs may be used. Alkanethiols are molecules with an alkyl chain as the back bone, a tail group, and an S—H head group. Thiols may be used on noble metal interface layers due to the strong affinity of sulfur for these metals. Examples of thiol-based SAMs that may be used include, but are not limited to, 1-dodecanethiol (DDT), 11-mercaptoundecanoic acid (MUA), and hydroxyl-terminated (hexaethylene glycol) undecanethiol (1-UDT). These thiols contain the same backbone, but different end groups—namely, methyl ($CH_3$), carboxyl (COOH), and hydroxyl-terminated hexaethylene glycol (HO—$(CH_2CH_2O)_6$) for DDT, MUA, and 1-UST, respectively. In certain embodiments, SAMs may be formed by incubating gold surfaces in thiol solutions using a suitable solvent, such as anhydrous ethanol.

Following formation of a SAM, the SAM may be biologically functionalized, such as by receiving at least one functionalization (e.g., specific binding) material. In certain embodiments, specific binding materials may be applied on or over a SAM using a microarray spotting needle or other suitable methods. In certain embodiments, an interface layer may be patterned (e.g., using photolithography and selective etching for defining the interface layer) with a high dimensional tolerance over only a portion of a resonator structure (which includes a substrate), a SAM may be applied over the interface layer, and a subsequently applied specific binding material attaches only to the SAM. In certain embodiments, patterning of an interface layer may provide a higher dimensional tolerance for positioning of the specific binding material than could be attained by microarray spotting alone. Examples of specific binding materials include, but are not limited to, antibodies, receptors, ligands, and the like. A specific binding material is preferably configured to receive a predefined target species (e.g., molecule, protein, DNA, virus, bacteria, etc.). Functionalization material including specific binding material may include a thickness in a range of from about 5 nm to about 1000 nm, or from about 5 nm to about 500 nm. In certain embodiments, an array of different specific binding materials may be provided over different active areas of a multi-resonator structure (i.e., one or more resonator structures including multiple active regions), optionally in combination with one or more active areas that are devoid of specific binding materials to serve as comparison (or "reference") regions. In certain embodiments, a functionalization material (e.g., bio-functionalization) may provide non-specific binding utility.

In certain embodiments, a bulk acoustic wave MEMS resonator structure includes a piezoelectric material comprising aluminum nitride or zinc oxide material that includes a c-axis having an orientation distribution that is predominantly non-parallel (and may also be non-perpendicular) to normal of a face of the substrate. Such a c-axis orientation distribution enables creation of shear displacements, which beneficially enable operation of the MEMS resonator structure with liquids, such as in a sensor and/or microfluidic device. In certain embodiments, one or more piezoelectric material regions may include a c-axis with a longitudinal orientation, or a c-axis having an orientation distribution that is predominantly perpendicular to normal of a face of the substrate, to enable creation of longitudinal displacements that may be beneficial to promote mixing, agitation, and/or movement of fluid (or constituents such as analyte(s) contained therein).

Methods for forming hexagonal crystal structure piezoelectric materials including a c-axis having an orientation distribution that is predominantly non-parallel to normal of a face of a substrate are disclosed in U.S. patent application Ser. No. 15/293,063 filed on Oct. 13, 2016, with the foregoing application hereby being incorporated by reference herein. Additional methods for forming piezoelectric materials having an inclined c-axis orientation are disclosed in U.S. Pat. No. 4,640,756 issued on Feb. 3, 1987, with the foregoing patent hereby being incorporated by reference herein.

Certain embodiments are directed to a fluidic device including multiple bulk acoustic wave MEMS resonator structures as disclosed herein and including a fluidic passage (e.g., a channel, a chamber, or the like) arranged to conduct a liquid to contact at least one functionalization (e.g., specific binding) material arranged over at least one active region of the resonator structures. Such a device may be microfluidic in scale, and comprise at least one microfluidic channel (e.g., having at least one dimension, such as height and/or width, of no greater than about 500 microns, or about 250 microns, or about 100 microns). For example, following fabrication of a bulk acoustic wave MEMS resonator structures and deposition of an interface layer and a SAM over portions thereof (optionally preceded by deposition of a hermeticity layer), a microfluidic device may be fabricated by forming one or more walls defining lateral boundaries of a microfluidic channel over a first bulk acoustic wave MEMS resonator structure with the active region thereof arranged along a bottom surface of the microfluidic channel, and then enclosing the microfluidic channel using a second bulk acoustic wave resonator structure with the active region thereof arranged along a top surface of the microfluidic channel. In certain embodiments, functionalization (e.g., specific binding) material may be pre-applied to the active region of each bulk acoustic wave MEMS resonator structure before formation of the microfluidic channel; in other embodiments, functionalization material may be applied over active regions of the bulk acoustic wave resonator structure following formation of the microfluidic channel. Walls of a microfluidic channel may be formed of any suitable material, such as laser-cut "stencil" layers of thin polymeric materials and/or laminates, optionally including one or more self-adhesive surfaces (e.g., adhesive tape). Optionally such walls may be formed prior to deposition of a SAM layer, functionalization material, and/or blocking layers, with an SU-8 negative epoxy resist or other photoresist material. In certain embodiments, a cover or cap layer may be integrally formed with one or more walls (e.g., via molding or another suitable process) to define a portion of an upper boundary as well as lateral boundaries of at least one fluidic channel, and the integrally formed partial cover/wall structure may be applied (e.g., adhered or otherwise bonded) over at least a portion of a bulk acoustic wave resonator structure to enclose the at least one fluidic channel. In certain embodiments, functionalization (e.g., specific binding) material may be pre-applied to the active region of a bulk acoustic wave resonator structure before formation of a microfluidic passage; in other embodiments, functionalization material may be applied over an active region of a bulk acoustic wave resonator structure following formation of the microfluidic passage.

In certain embodiments, a chemical or biological blocking material may be applied over a portion of a SAM to prevent attachment of a functionalization (e.g., specific binding) material over one or more selected regions of a BAW resonator structure (e.g., one or more regions apart from an active region). The proper choice of a chemical or biological blocking material (e.g., blocking buffer) for a given analysis depends on the type of target species or analyte present in a sample. Various types of blocking buffers such as highly purified proteins, serum, or milk may be used to block free sites on a SAM. Additional blockers include ethanolamine or poly(ethylene oxide) [PEO]—containing materials. An ideal blocking buffer would bind to all potential sites of non-specific interaction away from an active region. To optimize a blocking buffer for a particular analysis, empirical testing may be used to determine signal-to-noise ratio.

No single chemical blocking material is ideal for every situation, since each antibody-antigen pair has unique characteristics.

Figure 3:
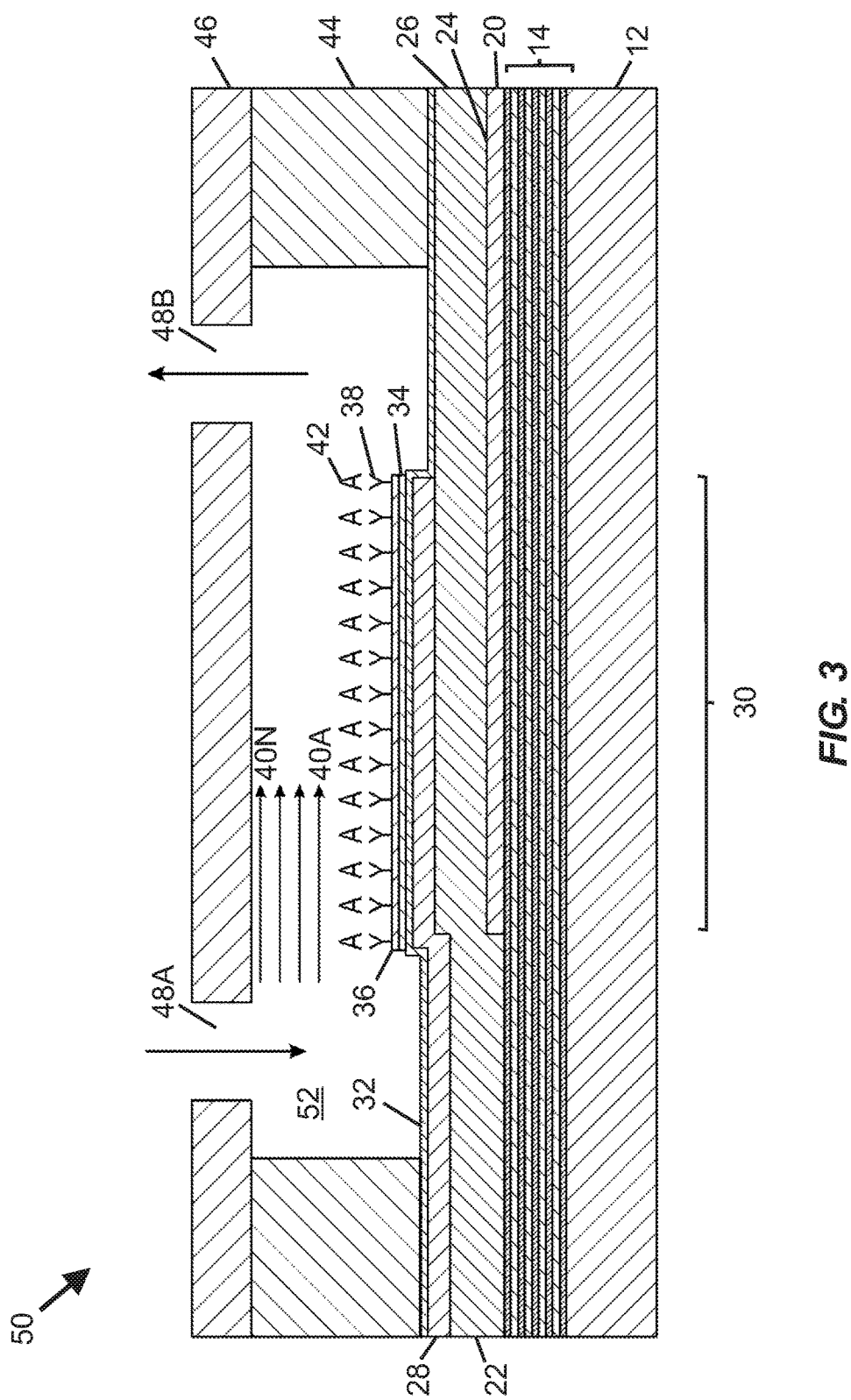
FIG. 3 is a schematic cross-sectional view of a portion of a fluidic device (e.g., a biochemical sensor device) including a microfluidic channel bounded from below by a BAW resonator structure, bounded laterally by walls, and bounded from above by a cover defining fluidic ports, to serve as a comparison device intended to provide context for subsequently described embodiments of the present disclosure.

FIG. 3 is a schematic cross-sectional view of a portion of a fluidic device 50 (e.g., a biochemical sensor device) including a microfluidic channel 52 bounded from below by a bulk acoustic wave MEMS resonator structure including an active region 30, bounded laterally by walls 44, and bounded from above by a cover or cap layer 46 defining fluidic ports 48A, 48B to serve as a comparison device intended to provide context for subsequently described embodiments of the present disclosure. The fluidic device 50 includes a substrate 12 overlaid with an acoustic reflector 14, and a bottom side electrode 20 arranged generally below a piezoelectric material 22. A top side electrode 28 (which may be referred to as a "proximal electrode" as being closer to a fluid interface than the bottom side electrode 20) extends over a portion of the piezoelectric material 22, wherein a portion of the piezoelectric material 22 arranged between the top side electrode 28 and the bottom side electrode 20 embodies an active region 30 of the BAW resonator structure. The bottom side electrode 20 may be referred to as a "distal electrode" as being more distant from a fluid interface than the top side electrode 28. The top side electrode 28 and the piezoelectric material 22 are overlaid with a hermeticity layer 32, an interface layer 34, and a self-assembled monolayer (SAM) 36. Portions of the SAM 36 extending away from the active region 30 may optionally be overlaid with a chemical or biological blocking material (not shown) to prevent attachment of specific binding material. A portion of the SAM 36 registered with the active region 30 is overlaid with functionalization (e.g., specific binding) material 38 arranged to bind a specified analyte. Walls 44 that are laterally displaced from the active region 30 extend upward from the hermeticity layer 32 to define lateral boundaries of the microfluidic channel 52 containing the active region 30. Such walls 44 may be formed of any suitable material, such as a laser-cut "stencil" layer of thin polymeric materials and/or laminate materials, optionally including one or more self-adhesive surfaces (e.g. adhesive tape). Optionally such walls 44 may be formed prior to deposition of the SAM 36, functionalization material 38, and any optionally applied chemical or biological blocking material (not shown) with an SU-8 negative epoxy resist or other photoresist material. If the walls 44 are formed on the SAM 36, the SAM 36 may promote adhesion of the walls 44. The cover or cap layer 46 defining upper surface fluidic ports 48A, 48B is further provided to provide an upper boundary for the microfluidic channel 52. The cover or cap layer 46 may be formed by defining ports (e.g., via laser cutting or water jet cutting) in a layer of an appropriate material (e.g., a substantially inert polymer, glass, silicon, ceramic, or the like), and adhering the cover or cap layer 46 to top surfaces of the walls 44.

In use of the fluidic device 50, a fluid sample may be supplied through the first fluidic port 48A into the microfluidic channel 52 over the active region 30 and through the second fluidic port 48B to exit the microfluidic channel 52. Due to the laminar nature of the fluid flow within the microfluidic channel 52, the fluid volume may be modeled and behave as a "stack" of horizontal fluid layers including a lowermost fluid layer 40A and an uppermost fluid layer 40N. An analyte 42 contained in the lowermost fluid layer 40A of the fluid sample is bound to the functionalization (e.g., specific binding) material 38; however, analyte contained in fluid layers above the lowermost fluid layer 40A (including the uppermost fluid layer 40N) may not be available to bind with the functionalization material 38, since diffusion of analyte (e.g., in a vertical direction) between the fluid layers 40A-40N occurs slowly. As a result, analyte binding rate is limited, and an extended time may be necessary to complete a desired measurement of a sample. With respect to analyte from the lowermost fluid layer 40A that is bound to the functionalization material 38, when a bulk acoustic wave is induced in the active region 30 by supplying an electrical (e.g., alternating current) signal to the bottom and top side electrodes 20, 28, detection of a change in at least one of a frequency property, an amplitude magnitude property, or a phase property of the BAW resonator structure indicates a presence and/or quantity of target species (i.e., analyte) bound to the functionalization material 38.

Figure 4:
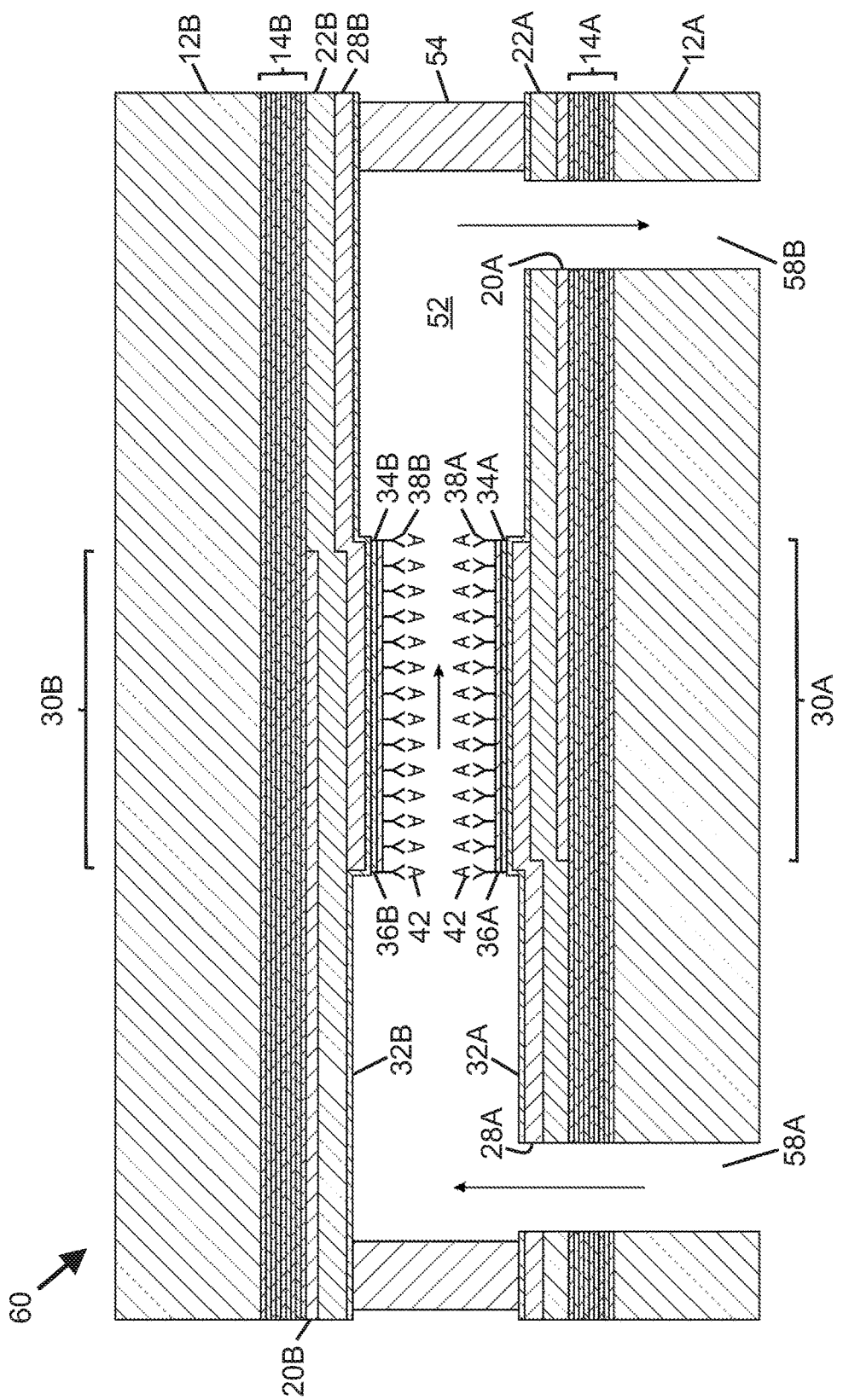
FIG. 4 is a schematic cross-sectional view of a portion of a fluidic device (e.g., a biochemical sensor device) including a microfluidic channel extending between first and second opposing BAW resonator structures, with fluidic vias extending through a first substrate supporting the first BAW resonator structure, and with functionalization material provided on or over an active region of each BAW resonator structure, according to one embodiment of the present disclosure.

FIG. 4 is a schematic cross-sectional view of a portion of a fluidic device 60 (e.g., a biochemical sensor device) including a microfluidic channel 52 extending between first and second opposing BAW MEMS resonator structures with functionalization material provided on or over the active region of each resonator, according to one embodiment of the present disclosure. Each BAW resonator structure is preferably configured to exhibit a dominant shear response upon application of an alternating current signal across electrodes thereof. The presence of bulk acoustic wave MEMS resonator structures with functionalization material on or along opposing surfaces of the microfluidic channel 52 permits a functionalization material to interact with analyte borne by a greater number of fluid "layers" (e.g., including upper and lower fluid layers) flowing within the microfluidic channel 52, thereby increasing analyte binding rate, even in the absence of structures or methods that might otherwise promote mixing or agitation within the microfluidic channel 52. A first bulk acoustic wave MEMS resonator structure includes a first substrate 12A, a first acoustic reflector 14A arranged over the first substrate 12A, and a first distal electrode 20A and a first proximal electrode 28A arranged along opposing surfaces of a first piezoelectric material 22A overlying the first acoustic reflector 14A, wherein a portion of the first piezoelectric material 22A arranged between the first distal electrode 20A and the first proximal electrode 28A forms a first active region 30A. The proximal electrode 28A and the first piezoelectric layer 22A are overlaid with a first hermeticity layer 32A, and a central portion of the first hermeticity layer 32A is overlaid in a sequential fashion with a first interface layer 34A, a SAM 36A, and a first functionalization material 38A. Fluidic inlet and outlet vias 58A, 58B extending through the first substrate 12 and overlying layers enable fluid to be supplied from a bottom side of the fluidic device 60 to the microfluidic channel 52. The microfluidic channel 52 is bounded laterally by walls 54 that extend upward from the first hermeticity layer 32A. The microfluidic channel 52 is further bounded from above by a second bulk acoustic wave MEMS resonator structure that includes a second substrate 12B, a second acoustic reflector 14B arranged proximate to the second substrate 12B, and a second distal electrode 20B and a second proximal electrode 28B arranged along opposing surfaces of a second piezoelectric material 22B overlying the second acoustic reflector 14B, wherein a portion of the second piezoelectric material 22B arranged between the second distal electrode 20B and the second proximal electrode 28B forms a second active region 30B. The second proximal electrode 28B and the second piezoelectric layer 22B are overlaid with a second hermeticity layer 32B, and a central portion of the second hermeticity layer 32B is overlaid in a sequential fashion with a second interface layer 34B, a second SAM 36B, and a second functionalization material 38B.

In use of the fluidic device 60, a fluid sample may be supplied through the first fluidic via 58A into the microfluidic channel 52 over the active regions 30A, 30B to interact with the first and second functionalization materials 38A, 38B, and through the second fluidic via 58B to exit the microfluidic channel 52. At least one analyte 42 contained in the fluid sample is bound to the first functionalization material 38A proximate to the first active region 30A along a bottom surface of the microfluidic channel 52 and is bound to the second functionalization material 38B proximate to the second active region 30B along a top surface of the microfluidic channel 52. First and second bulk acoustic waves are induced in the first and second active regions 30A, 30B by supplying electrical (e.g., alternating current) signals to the first pair of electrodes 20A, 28A and the second pair of electrodes 20B, 28B, respectively, and detection of a change in frequency, amplitude magnitude, and/or phase properties of the first and second BAW resonator structures indicates a presence and/or quantity of target species (i.e., analyte 42) bound to the first and second functionalization materials 38A, 38B, respectively.

Figure 5:
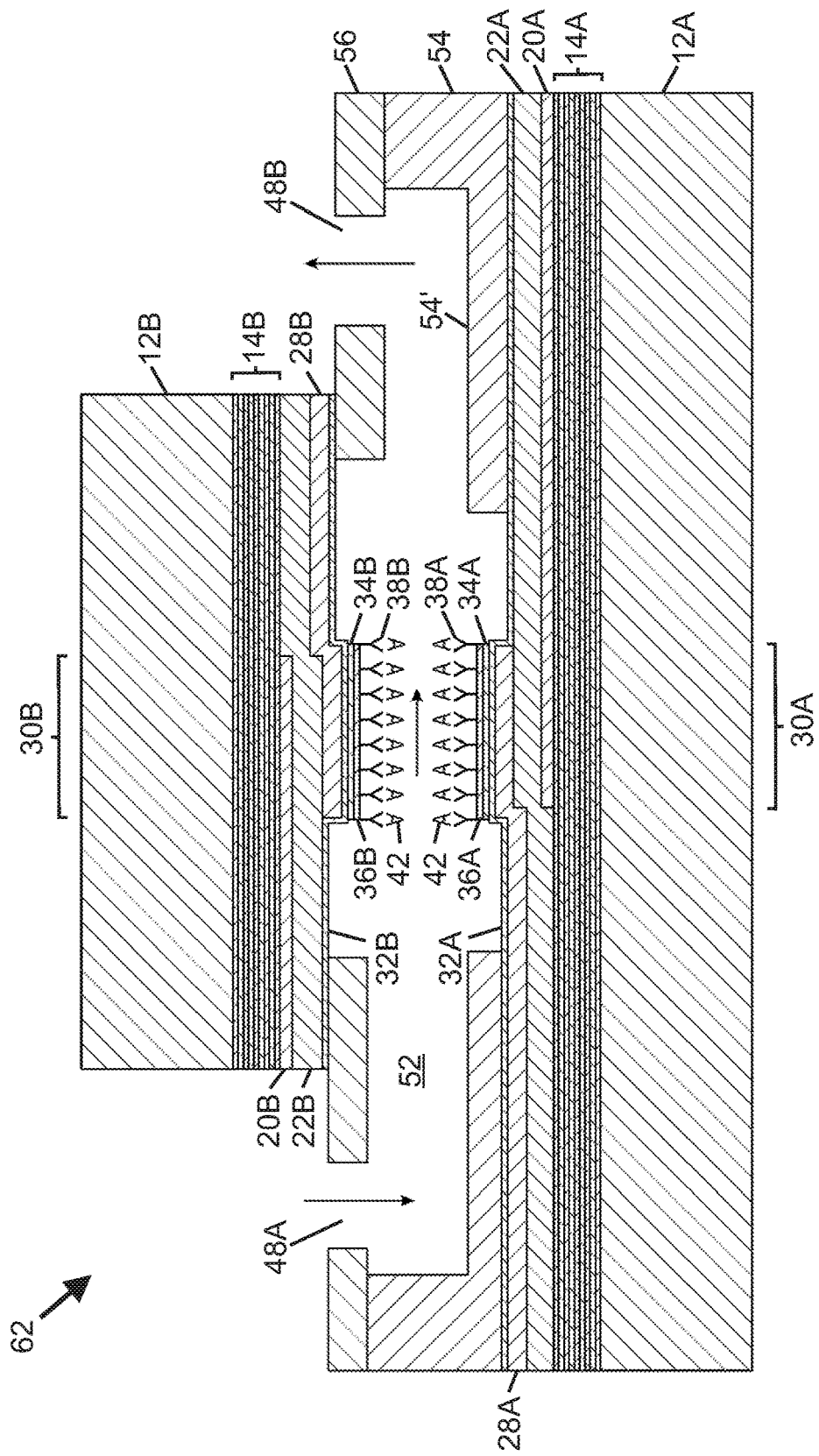
FIG. 5 is a schematic cross-sectional view of a portion of a fluidic device (e.g., a biochemical sensor device) including a microfluidic channel extending between first and second opposing BAW resonator structures supported by different substrates, with channel-defining intermediate layers extending laterally beyond one substrate and defining fluidic ports for accessing the channel, and with functionalization material provided on or over an active region of each BAW resonator structure, according to one embodiment of the present disclosure.

FIG. 5 is a schematic cross-sectional view of a portion of a fluidic device 62 (e.g., a biochemical sensor device) including a microfluidic channel 52 extending between first and second opposing BAW MEMS resonator structures with functionalization material provided by one or over the active region of each resonator, and with intermediate layers defining portions of the microfluidic channel 52 extending laterally beyond one substrate and defining fluidic ports for accessing the microfluidic channel, according to one embodiment of the present disclosure. Each BAW resonator structure is preferably configured to exhibit a dominant shear response upon application of an alternating current signal across the electrodes thereof. The presence of bulk acoustic wave MEMS resonator structures with functionalization material on or along opposing surfaces of the microfluidic channel 52 permits a functionalization material to interact with analyte borne by a greater number of fluid "layers" (e.g., including upper and lower fluid layers) flowing within the channel 52, thereby increasing analyte binding rate. A first bulk acoustic wave MEMS resonator structure includes a first substrate 12A, a first acoustic reflector 14A arranged over the first substrate 12A, and a first distal electrode 20A and a first proximal electrode 28A arranged along opposing surfaces of a first piezoelectric material 22A overlying the first acoustic reflector 14A, wherein a portion of the first piezoelectric material 22A arranged between the first distal electrode 20A and the first proximal electrode 28A forms a first active region 30A. The proximal electrode 28A and the first piezoelectric layer 22A are overlaid with a first hermeticity layer 32A, and a central portion of the first hermeticity layer 32A is overlaid in a sequential fashion with a first interface layer 34A, a first SAM 36A, and a first functionalization material 38A. The microfluidic channel 52 is bounded laterally by walls 54 that extend upward from the first hermeticity layer 32A, with wall extensions 54' extending laterally inward over the first hermeticity layer 32A along lower portions of the microfluidic channel 52. The microfluidic channel 52 is bounded from above in part by a cover layer 56 that defines fluidic ports 48A, 48B in fluid communication with the microfluidic channel 52. The microfluidic channel 52 is further bounded from above in part by a second bulk acoustic wave MEMS resonator structure that includes a second substrate 12B, a second acoustic reflector 14B arranged proximate to the second substrate 12B, and a second distal electrode 20B and a second proximal electrode 28B arranged along opposing surfaces of a second piezoelectric material 22B overlying the second acoustic reflector 14B, wherein a portion of the second piezoelectric material 22B arranged between the second distal electrode 20B and the second proximal electrode 28B forms a second active region 30B. The second proximal electrode 28B and the second piezoelectric layer 22B are overlaid with a second hermeticity layer 32B, and a central portion of the second hermeticity layer 32B is overlaid in a sequential fashion with a second interface layer 34B, a SAM 36B, and a second functionalization material 38B. Providing the walls 54 and cover layer 56 extending laterally beyond the second substrate 12B permits the fluidic ports 48A, 48B to be defined through the cover layer 56 without requiring drilling through the second substrate 12B.

In use of the fluidic device 62, a fluid sample may be supplied through the first fluidic port 48A into the microfluidic channel 52 over the active regions 30A, 30B to interact with the first and second functionalization materials 38A, 38B, and through the second fluidic port 48B to exit the microfluidic channel 52. At least one analyte 42 contained in the fluid sample is bound to the first functionalization material 38A proximate to the first active region 30A along a bottom surface of the microfluidic channel 52 and is bound to the second functionalization material 38B proximate to the second active region 30B along a top surface of the microfluidic channel 52. First and second bulk acoustic waves are induced in the first and second active regions 30A, 30B by supplying electrical (e.g., alternating current) signals to the first pair of electrodes 20A, 28A and the second pair of electrodes 20B, 28B, respectively, and detection of a change in frequency, amplitude magnitude, and/or phase properties of the first and second BAW resonator structures indicates a presence and/or quantity of target species (i.e., analyte 42) bound to the first and second functionalization materials 38A, 38B, respectively.

Although FIGS. 4 and 5 illustrate active regions 30A, 30B along opposing channel surfaces as being overlaid with functionalization material and being registered with one another at substantially the same distance from an upstream end of a microfluidic channel 52, it is to be appreciated that in certain embodiments, active regions of different resonators may lack functionalization material and/or may be located at different distances from an upstream end of a microfluidic channel. In certain embodiments, one or more channel surfaces may include multiple active regions. Additionally, in certain embodiments, one or more BAW resonator structures may be arranged to exhibit a dominant shear response upon application of an alternating current signal across the electrodes thereof, and/or one or more other BAW resonator structures may be arranged to exhibit a dominant longitudinal response upon application of an alternating current signal across electrodes thereof.

Figure 6:
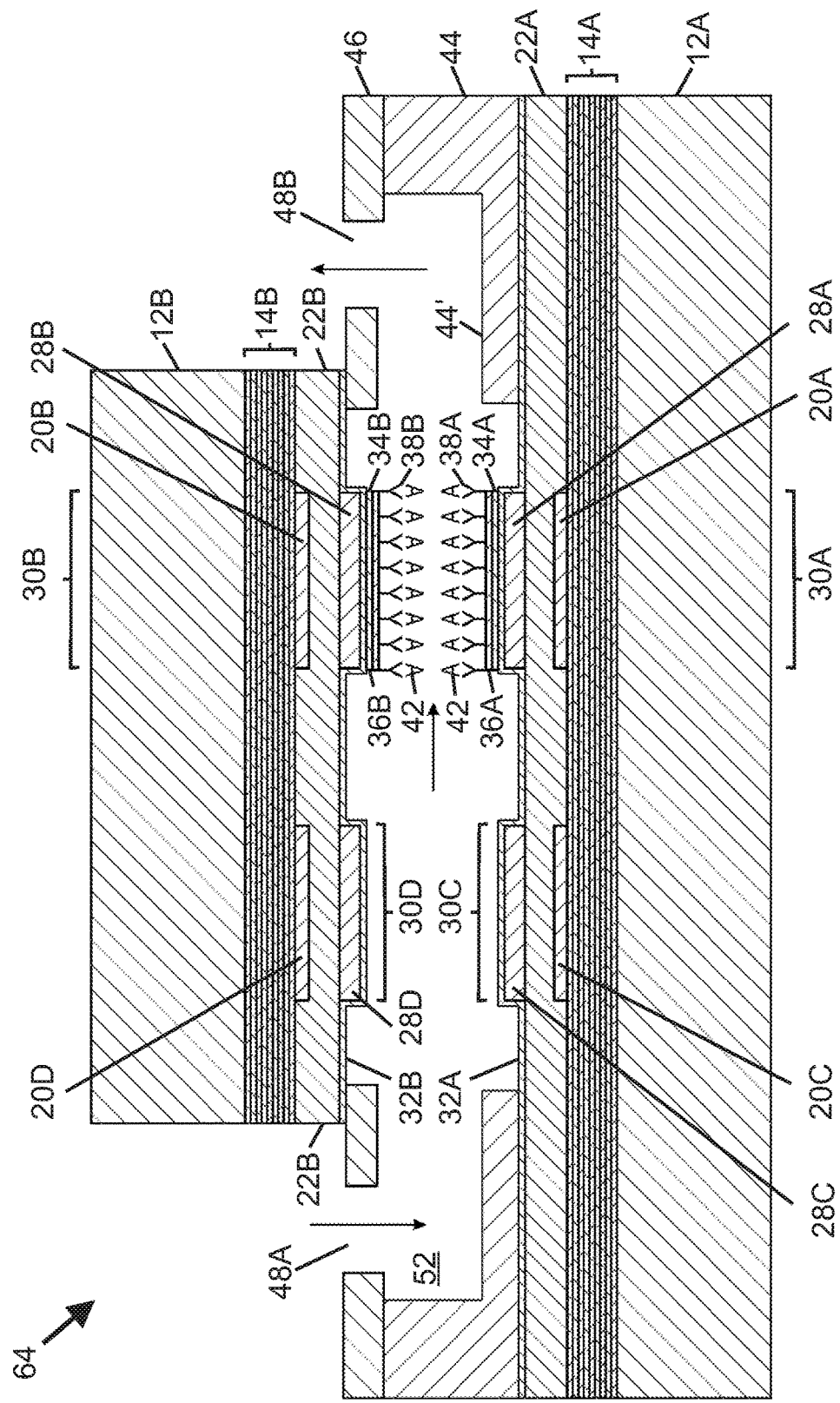
FIG. 6 is a schematic cross-sectional view of a portion of a fluidic device (e.g., a biochemical sensor device) including a microfluidic channel extending two pairs of opposing BAW resonator structures supported by two substrates, with channel-defining intermediate layers extending laterally beyond one substrate and defining fluidic ports for accessing the channel, and with functionalization material provided on or over an active regions of one pair of opposing BAW resonator structures, according to one embodiment of the present disclosure.

FIG. 6 is a schematic cross-sectional view of a portion of a fluidic device 64 (e.g., a biochemical sensor device) including a microfluidic channel 52 extending two pairs of opposing BAW resonator structures supported by two substrates 12A, 12B, with intermediate channel-defining layers—walls 44 and cover or cap layer 46 and wall extensions 44'—defining portions of the microfluidic channel 52 extending laterally beyond one substrate 12B and defining fluidic ports 48A, 48B for accessing the microfluidic channel, with different pairs of BAW resonator structures providing different functionality, according to one embodiment of the present disclosure. In certain embodiments, an upstream first pair of opposing BAW resonator structures includes resonators devoid of functionalization material and preferably configured to exhibit a dominant longitudinal response upon application of an alternating current signal across electrodes thereof, and a downstream second pair of opposing BAW resonator structures includes resonators with active regions overlaid with functionalization material and preferably configured to exhibit a dominant shear response upon application of an alternating current signal across electrodes thereof. The presence of upstream BAW resonator structures configured to exhibit a dominant longitudinal response may enable mixing, agitation, or movement of fluid and/or target species contained therein, while the presence of downstream BAW resonator structures overlaid with functionalization material, configured to exhibit a dominant shear response, and arranged along opposing surfaces of the microfluidic channel 52, enables detection of presence or quantity of target species supplied by fluid in the microfluidic channel 52 with an enhanced analyte binding rate compared with use of one or two functionalized BAW resonators arranged along a single channel surface.

As shown in FIG. 6, a first bulk acoustic wave MEMS resonator structure includes a first substrate 12A, a first acoustic reflector 14A arranged over the first substrate 12A, and a first distal electrode 20A and a first proximal electrode 28A arranged along opposing surfaces of a first piezoelectric material 22A overlying the first acoustic reflector 14A, wherein a portion of the first piezoelectric material 22A arranged between the first distal electrode 20A and the first proximal electrode 28A forms a first active region 30A. The proximal electrode 28A and the first piezoelectric layer 22A are overlaid with a first hermeticity layer 32A, and a portion of the first hermeticity layer 32A coincident with the first active region 30A is overlaid in a sequential fashion with a first interface layer 34A, a first SAM 36A, and a first functionalization material 38A. A second BAW MEMS resonator structure includes a second substrate 12B, a second acoustic reflector 14B arranged proximate to the second substrate 12B, and a second distal electrode 20B and a second proximal electrode 28B arranged along opposing surfaces of a second piezoelectric material 22B overlying the second acoustic reflector 14B, wherein a portion of the second piezoelectric material 22B arranged between the second distal electrode 20B and the second proximal electrode 28B forms a second active region 30B. The second proximal electrode 28B and the second piezoelectric layer 22B are overlaid with a second hermeticity layer 32B, and portion of the second hermeticity layer 32B coincident with the second active region 30B is overlaid in a sequential fashion with a second interface layer 34B, a SAM 36B, and a second functionalization material 38B. The first active region 30A arranged along a bottom surface of the microfluidic channel generally opposes the second active region 30B arranged along a top surface of the microfluidic channel 52. The first and second active regions 30A, 30B are preferably configured to exhibit a dominant shear response upon application of alternating current signals across the electrode pairs 20A, 28A and 20B, 28B.

With further reference to FIG. 6, a second pair of bulk acoustic wave MEMS resonators includes third and fourth bulk acoustic wave MEMS resonator structures arranged on opposing bottom and top surfaces of the microfluidic channel 52 and arranged upstream of the first and second bulk acoustic wave MEMS resonator structures. The third bulk acoustic wave MEMS resonator structure overlies the first substrate 12A and the first acoustic reflector 14A, and includes a third distal electrode 20C and a third proximal electrode 28C, with a portion of the first piezoelectric material 22A between the third distal electrode 20C and the third proximal electrode 28C embodying a third active region 30C. The fourth bulk acoustic wave MEMS resonator structure overlies the second substrate 12B and the second acoustic reflector 14B, and includes a fourth distal electrode 20D and a fourth proximal electrode 28D, with a portion of the second piezoelectric material 22B between the fourth distal electrode 20D and the fourth proximal electrode 28D embodying a fourth active region 30D. As illustrated, the third and fourth active regions 30C, 30D include overlying hermeticity material layers 32A, 32B, but do not include any associated functionalization materials.

In use of the fluidic device 64, a fluid sample may be supplied through the first fluidic port 48A into the microfluidic channel 52, over the third and fourth active regions 30C, 30D, then over the first and second active regions 30A, 30B to interact with the first and second functionalization materials 38A, 38B, and through the second fluidic port 48B to exit the microfluidic channel 52. Third and fourth bulk acoustic waves are induced in the third and fourth active regions 30C, 30D by supplying electrical (e.g., alternating current) signals to the third distal and proximal electrodes 20C, 28C and the fourth distal and proximal electrodes 20D, 28D, respectively, to generate acoustic waves including at least significant longitudinal modes, thereby promoting mixing, agitation, and/or movement of fluid or constituents thereof in the microfluidic channel 52. Downstream of the third and fourth active regions 30C, 30D, at least one analyte 42 contained in the fluid sample is bound to the first functionalization material 38A proximate to the first active region 30A along a bottom surface of the microfluidic channel 52 and is bound to the second functionalization material 38B proximate to the second active region 30B along a top surface of the microfluidic channel 52. First and second bulk acoustic waves are induced in the first and second active regions 30A. 30B by supplying electrical (e.g., alternating current) signals to the first pair of electrodes 20A, 28A and the second pair of electrodes 20B, 28B, respectively, and detection of a change in frequency, amplitude magnitude, and/or phase properties of the first and second bulk acoustic wave resonator structures indicates a presence and/or quantity of target species (i.e., analyte 42) bound to the first and second functionalization materials 38A, 38B, respectively.

Figure 7:
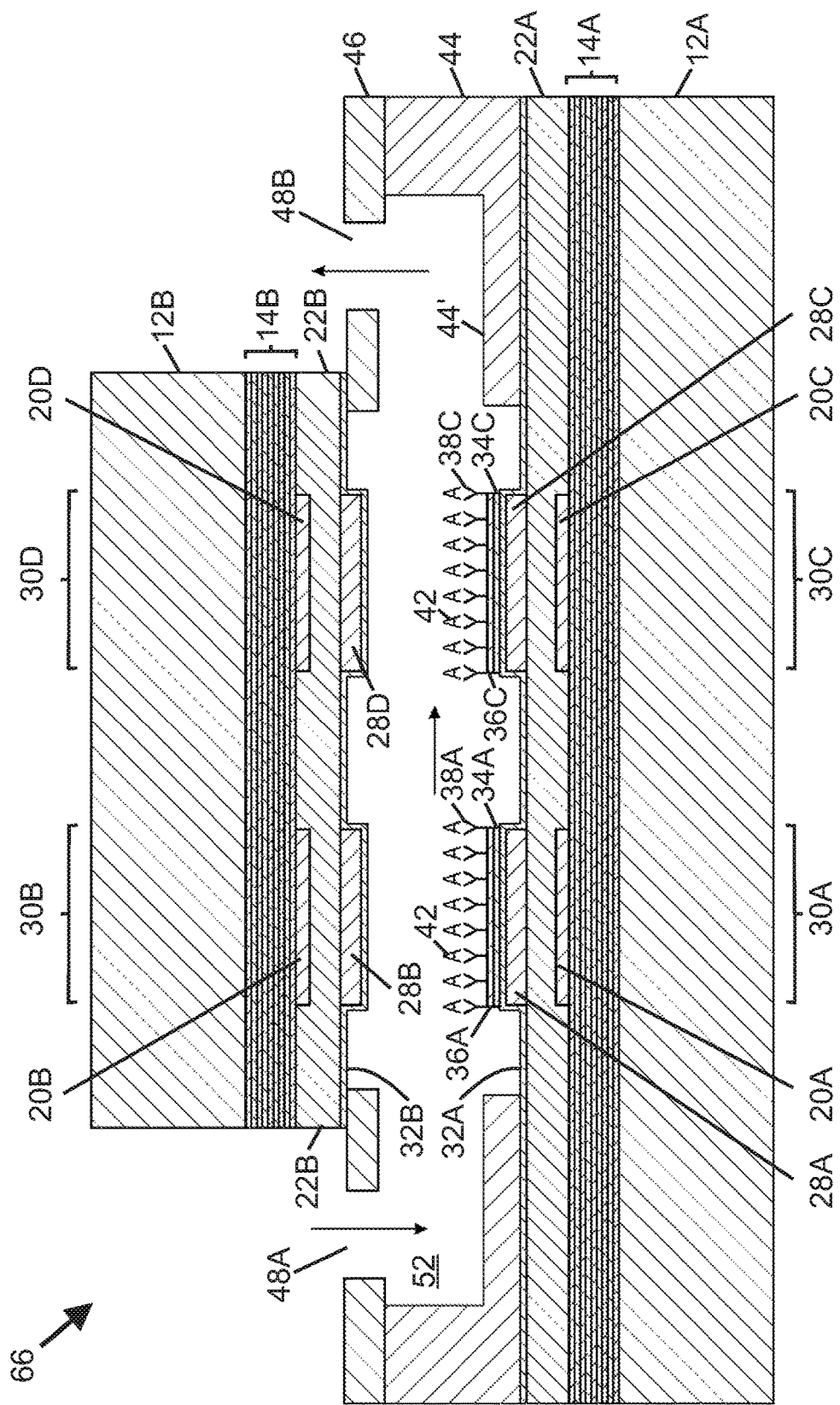
FIG. 7 is a schematic cross-sectional view of a portion of a fluidic device (e.g., a biochemical sensor device) including a microfluidic channel extending two pairs of opposing BAW resonator structures supported by two substrates, with channel-defining intermediate layers extending laterally beyond one substrate and defining fluidic ports for accessing the channel, and with functionalization material provided on or over an active regions of one BAW resonator structure in each pair of opposing BAW resonator structures, according to one embodiment of the present disclosure.

FIG. 7 is a schematic cross-sectional view of a portion of a fluidic device (e.g., a biochemical sensor device) including a microfluidic channel 52 extending two pairs of opposing BAW resonator structures supported by two substrates 12A, 12B, with intermediate channel-defining layers (i.e., walls 44 and cover or cap layer 46 and wall extensions 44') defining portions of the microfluidic channel 52 extending laterally beyond one substrate 12B and defining fluidic ports 48A, 48B for accessing the microfluidic channel, according to one embodiment of the present disclosure. An upstream first pair and a downstream second pair of opposing BAW resonator structures each include one resonator overlaid with functionalization material (and preferably configured to exhibit a dominant shear response upon application of an alternating current signal across electrodes thereof) and another resonator devoid of functionalization material (and preferably configured to exhibit a dominant longitudinal response upon application of an alternating current signal across electrodes thereof). The presence of BAW resonator structures configured to exhibit a dominant longitudinal response may enable mixing, agitation, or movement of fluid and/or target species proximate to an opposing BAW resonator structure overlaid with functionalization material and configured to exhibit dominant shear response. Such configuration may enhance promote enhanced analyte binding rate compared to use of one or two functionalized BAW resonator structures arranged along a single channel surface without non-functionalized BAW resonator structures arranged along an opposing channel surface.

As shown in FIG. 7, a first bulk acoustic wave MEMS resonator structure includes a first substrate 12A, a first acoustic reflector 14A arranged over the first substrate 12A, and a first distal electrode 20A and a first proximal electrode 28A arranged along opposing surfaces of a first piezoelectric material 22A overlying the first acoustic reflector 14A, wherein a portion of the first piezoelectric material 22A arranged between the first distal electrode 20A and the first proximal electrode 28A forms a first active region 30A. The proximal electrode 28A and the first piezoelectric layer 22A are overlaid with a first hermeticity layer 32A, and a portion of the first hermeticity layer 32A coincident with the first active region 30A is overlaid in a sequential fashion with a first interface layer 34A, a first SAM 36A, and a first functionalization material 38A. A second bulk acoustic wave MEMS resonator structure includes a second substrate 12B, a second acoustic reflector 14B arranged proximate to the second substrate 12B, and a second distal electrode 20B and a second proximal electrode 28B arranged along opposing surfaces of a second piezoelectric material 22B overlying the second acoustic reflector 14B, wherein a portion of the second piezoelectric material 22B arranged between the second distal electrode 20B and the second proximal electrode 28B forms a second active region 30B. The second proximal electrode 28B and the second piezoelectric layer 22B are overlaid with a second hermeticity layer 32B but are devoid of any functionalization material. The first active region 30A arranged along a bottom surface of the microfluidic channel generally opposes the second active region 30B arranged along a top surface of the microfluidic channel 52. The first active region 30A is preferably configured to exhibit a dominant shear response upon application of alternating current signals across the first distal electrode 20A and the first proximal electrode 28A. The second active region 30B is preferably configured to exhibit a dominant longitudinal response upon application of alternating current signals across the second distal electrode 20B and the second proximal electrode 28B.

With further reference to FIG. 7, a second pair of bulk acoustic wave MEMS resonator structures includes third and fourth bulk acoustic wave MEMS resonator structures arranged on opposing bottom and top surfaces of the microfluidic channel 52 and arranged downstream of the first and second bulk acoustic wave MEMS resonator structures. The third bulk acoustic wave MEMS resonator structure overlies the first substrate 12A and the first acoustic reflector 14A, and includes a third distal electrode 20C and a third proximal electrode 28C, with a portion of the first piezoelectric material 22A between the third distal electrode 20C and the third proximal electrode 28C embodying a third active region 30C. The proximal electrode 28C and the first piezoelectric layer 22A are overlaid with the first hermeticity layer 32A, and a portion of the first hermeticity layer 32A coincident with the third active region 30C is overlaid in a sequential fashion with a third interface layer 34C, a third SAM 36C, and a third layer of functionalization material 38C. The fourth bulk acoustic wave MEMS resonator structure overlies the second substrate 12B and the second acoustic reflector 14B, and includes a fourth distal electrode 20D and a fourth proximal electrode 28D, with a portion of the second piezoelectric material 22B between the fourth distal electrode 20D and the fourth proximal electrode 28D embodying a fourth active region 30D. The fourth proximal electrode 28D and the second piezoelectric layer 22B are overlaid with a second hermeticity layer 32B, do not include any associated functionalization materials.

In use of the fluidic device 66, a fluid sample may be supplied through the first fluidic port 48A into the microfluidic channel 52, over the first and second active regions 30A, 30B (including interaction with the first functionalization material 38A), and then over the third and fourth active regions 30C, 30D (including interaction with the third functionalization material 38C) and through the second fluidic port 48B to exit the microfluidic channel 52. Second and fourth bulk acoustic waves are induced in the second and fourth active regions 30B, 30D along a top surface of the microfluidic channel 52 by supplying electrical (e.g., alternating current) signals to the second distal and proximal electrodes 20B, 28B and the fourth distal and proximal electrodes 20D, 28D, respectively, to generate acoustic waves including at least significant longitudinal modes in the second and fourth active regions 30B, 30D, thereby promoting mixing, agitation, and/or movement of fluid or constituents thereof in the microfluidic channel 52. Additionally, first and third bulk acoustic waves are induced in the first and third active regions 30A, 30C by supplying electrical (e.g., alternating current) signals to the first distal and proximal electrodes 20A, 28A and the third distal and proximal electrodes 20C, 28C, respectively, to generate acoustic waves including at least significant shear modes. Detection of a change in frequency, amplitude magnitude, and/or phase properties of the first and third bulk acoustic wave resonator structures indicates a presence and/or quantity of target species (i.e., analyte 42) bound to the first and third functionalization materials 38A, 38C, respectively.

Figure 8:
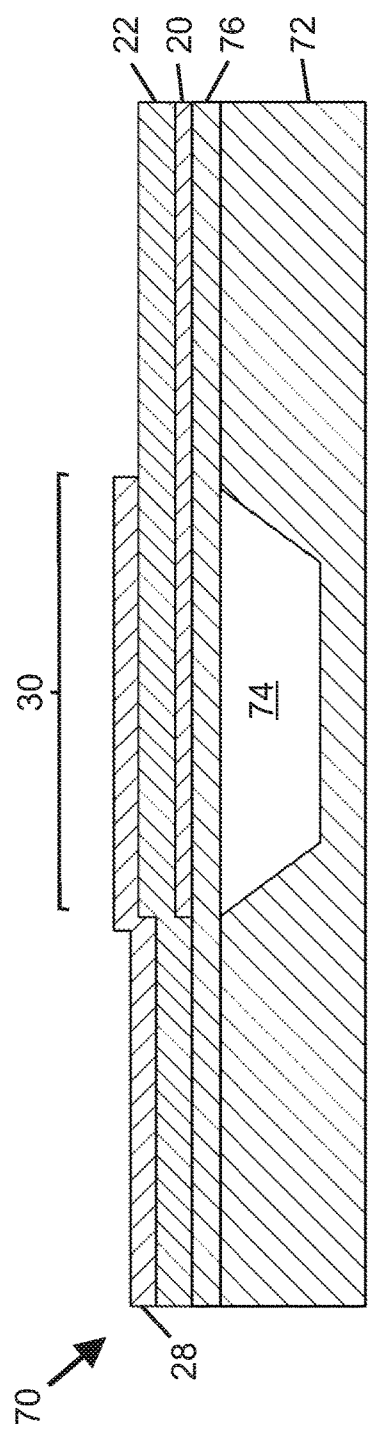
FIG. 8 is a schematic cross-sectional view of a film bulk acoustic wave resonator (FBAR) structure usable in devices according to certain embodiments, with the FBAR structure including an inclined c-axis hexagonal crystal structure piezoelectric material, a substrate defining a cavity covered by a support layer, and an active region registered with the cavity with a portion of the piezoelectric material arranged between overlapping portions of a top side electrode and a bottom side electrode.

Although the preceding figures illustrated various solidly mounted bulk acoustic wave MEMS resonator structures, it is to be appreciated that film bulk acoustic wave resonator (FBAR) structures may be employed in fluidic devices according to certain embodiments. FIG. 8 is a schematic cross-sectional view of a film bulk acoustic wave resonator (FBAR) structure 70 according to one embodiment including an inclined c-axis hexagonal crystal structure piezoelectric material 22 layer. The FBAR structure 70 includes a substrate 72 (e.g., silicon or another semiconductor material) defining a cavity 74 covered by a support layer 76 (e.g., silicon dioxide) and includes an active region 30 registered with the cavity 74 with a portion of the piezoelectric material 22 arranged between overlapping portions of a proximal electrode 28 and a distal electrode 20. The distal electrode 20 is arranged over a portion of the support layer 76. The distal electrode 20 and the support layer 76 are overlaid with the piezoelectric material 22 (e.g., embodying inclined c-axis hexagonal crystal structure piezoelectric material such as AlN or ZnO), and the proximal electrode 28 is arranged over at least a portion of a top surface of the piezoelectric material 22. A portion of the piezoelectric material 22 arranged between the proximal electrode 28 and the distal electrode 20 embodies the active region 30 of the FBAR structure 70. The active region 30 is arranged over and registered with the cavity 74 disposed below the support layer 76. The cavity 74 serves to confine acoustic waves induced in the active region 30 by preventing dissipation of acoustic energy into the substrate 72, since acoustic waves do not efficiently propagate across the cavity 74. In this respect, the cavity 74 provides an alternative to the acoustic reflectors 14 illustrated and described in connection with FIG. 1 and subsequent figures. In certain embodiments, the support layer 76 may be removed or omitted. Although the cavity 74 shown is bounded from below by a thinned portion of the substrate 72, in alternative embodiments at least a portion of the cavity 74 extends through an entire thickness of the substrate 72. Steps for forming the FBAR structure 70 may include defining the cavity 74 in the substrate 72, filling the cavity 74 with a sacrificial material (not shown), optionally followed by planarization of the sacrificial material, depositing the support layer 76 over the substrate 72 and the sacrificial material, removing the sacrificial material (e.g., by flowing an etchant through vertical openings defined in the substrate 72 or the support layer 76, or lateral edges of the substrate 72), depositing the distal electrode 20 over the support layer 76, growing (e.g., via sputtering or other appropriate methods) the piezoelectric material 22 and depositing the proximal electrode 28.

Figure 9:
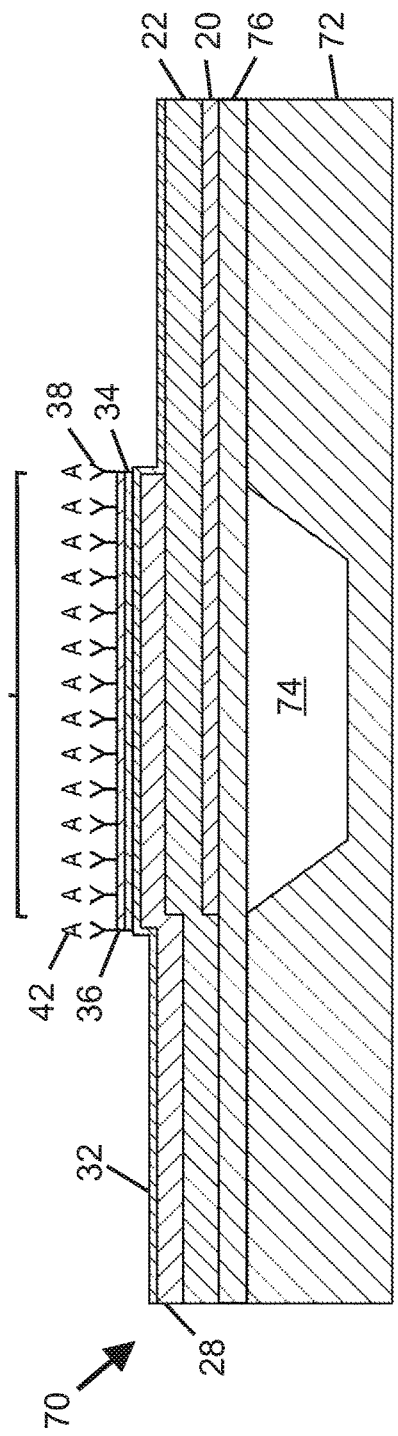
FIG. 9 is a schematic cross-sectional view of a FBAR structure according to FIG. 8, following addition of a hermeticity layer, an interface layer, a self-assembled monolayer, and a functionalization (e.g., specific binding) material over at least portions of the FBAR structure.

FIG. 9 is a schematic cross-sectional view of a FBAR structure 70 according to FIG. 8, following addition of hermeticity layer 32 over the proximal electrode 28 and the piezoelectric material 22 layer, and addition of an interface layer 34, a SAM 36, and a functionalization material 38 (e.g., specific binding material) over the active region 30. It is to be appreciated that multiple FBAR structures 70 as illustrated in FIG. 8 or 9 may be arranged along opposing surfaces of a fluidic (e.g., microfluidic) channel of a fluidic device according to various configurations disclosed previously herein, or according to configurations apparent to those skilled in the art upon reading the present disclosure.

One aspect of the disclosure relates to methods for biological or chemical sensing utilizing one or more fluidic devices as disclosed herein, according to steps disclosed herein. In certain embodiments, multiple acoustic waves may be induced in multiple active regions overlaid with functionalization material (which functionalization material may be compositionally the same or compositionally different among different active regions), and sensing a change in at least one of a frequency property, an amplitude magnitude property, or a phase property of the corresponding BAW resonator structures to indicate at least one of presence or quantity of target species bound to the functionalization material(s). In certain embodiments, a first bulk acoustic wave may be induced in a first active region configured to exhibit a dominant longitudinal response upon application of a first alternating current signal to promote at least one of mixing of the fluid or movement of a target species, and a second bulk acoustic wave may be induced in a second active region overlaid with functionalization material and configured to exhibit a dominant shear response upon application of a second alternating current signal, whereby change in at least one of a frequency property, an amplitude magnitude property, or a phase property of the second BAW resonator structure may be sensed to indicate at least one of presence or quantity of target species bound to the functionalization material.

Another aspect of the disclosure relates to a method for fabricating a fluidic device incorporating multiple BAW resonator structures, with at least one BAW resonator structure along a first surface of a fluidic channel and at least one second BAW resonator structure along a second surface of the fluidic channel opposing the first surface. In certain embodiments, a method includes fabricating first and second BAW resonator structures and arranging at least one intermediate layer defining lateral boundaries of a channel arranged to receive a fluid between the first BAW resonator structure and the second BAW resonator structure, wherein the first BAW resonator structure is arranged proximate to a first surface bounding the channel, the second BAW resonator structure is arranged proximate to a second surface bounding the channel, and the second surface opposes the first surface.

Those skilled in the art will recognize improvements and modifications to the preferred embodiments of the present disclosure. All such improvements and modifications are considered within the scope of the concepts disclosed herein and the claims that follow.

What is claimed is:

1. A fluidic device comprising:
   a channel arranged to receive a fluid;
   a first bulk acoustic wave resonator structure arranged between a first substrate and a first surface bounding the channel, wherein the first bulk acoustic wave resonator structure includes a first piezoelectric material, a first distal electrode arranged between the first piezoelectric material and the first substrate, and a first proximal electrode arranged between the first piezoelectric material and the channel, wherein at least a portion of the first piezoelectric material is arranged between the first distal electrode and the first proximal electrode to form a first active region; and
   a second bulk acoustic wave resonator structure arranged between a second substrate and a second surface bounding the channel, wherein the second surface opposes the first surface, and wherein the second bulk acoustic wave resonator structure includes a second piezoelectric material, a second distal electrode arranged between the second piezoelectric material and the second substrate, and a second proximal electrode arranged between the second piezoelectric material and the channel, wherein at least a portion of the second piezoelectric material is arranged between the second distal electrode and the second proximal electrode to form a second active region.

2. The fluidic device of claim 1, further comprising at least one intermediate layer defining at least a portion of the channel, wherein the at least one intermediate layer is arranged between the first bulk acoustic wave resonator structure and the second bulk acoustic wave resonator structure.

3. The fluidic device of claim 1, comprising at least one of the following features: the first piezoelectric material comprises a c-axis having an orientation distribution that is predominantly non-parallel to normal of a face of the first substrate; or the second piezoelectric material comprises a c-axis having an orientation distribution that is predominantly non-parallel to normal of a face of the second substrate.

4. The fluidic device of claim 1, wherein:
   the first piezoelectric material comprises a c-axis having an orientation distribution that is predominantly non-parallel to normal of a face of the first substrate, and the first bulk acoustic wave resonator structure is configured to exhibit a dominant shear response upon application of an alternating current signal across the first distal electrode and the first proximal electrode; and
   the second piezoelectric material comprises a c-axis having an orientation distribution that is predominantly non-parallel to normal of a face of the second substrate, and the second bulk acoustic wave resonator structure is configured to exhibit a dominant shear response upon application of an alternating current signal across the second distal electrode and the second proximal electrode.

5. A method for biological or chemical sensing, the method comprising:

supplying a fluid containing a target species into the channel of the fluidic device of claim 4, wherein said supplying is configured to cause at least some of the target species to bind to at least one first functionalization material arranged over the first active region, and to cause at least some of the target species to bind to at least one second functionalization material arranged over the second active region;

inducing a first bulk acoustic wave in the first active region, and sensing a change in at least one of a frequency, an amplitude, or a phase via the first bulk acoustic wave resonator structure to indicate at least one of presence or quantity of target species bound to the at least one first functionalization material; and inducing a second bulk acoustic wave in the second active region, and sensing a change in at least one of a frequency, an amplitude, or a phase via the second bulk acoustic wave resonator structure to indicate at least one of presence or quantity of target species bound to the at least one second functionalization material.

6. The fluidic device of claim 1, wherein:

the first bulk acoustic wave resonator structure is configured to exhibit a dominant longitudinal response upon application of an alternating current signal across the first distal electrode and the first proximal electrode; and the second piezoelectric material comprises a c-axis having an orientation distribution that is predominantly non-parallel to normal of a face of the second substrate, and the second bulk acoustic wave resonator structure is configured to exhibit a dominant shear response upon application of an alternating current signal across the second distal electrode and the second proximal electrode.

7. A method for biological or chemical sensing, the method comprising:

supplying a fluid containing a target species into the channel of the fluidic device of claim 6, wherein said supplying is configured to cause at least some of the target species to bind to at least one functionalization material arranged over the second active region;

inducing a first bulk acoustic wave in the first active region to promote at least one of mixing of the fluid or movement of the target species; and inducing a second bulk acoustic wave in the second active region, and sensing a change in at least one of a frequency, an amplitude, or a phase via the second bulk acoustic wave resonator structure to indicate at least one of presence or quantity of target species bound to the at least one functionalization material.

8. The fluidic device of claim 1, wherein the first bulk acoustic wave resonator structure comprises a first acoustic reflector structure arranged between the first substrate and the first distal electrode, and the second bulk acoustic wave resonator structure comprises a second acoustic reflector structure arranged between the second substrate and the second distal electrode.

9. The fluidic device of claim 1, wherein:

the first substrate defines a first cavity registered with an active region of the first bulk acoustic wave resonator structure, and the second substrate defines a second cavity registered with an active region of the second bulk acoustic wave resonator structure.

10. The fluidic device of claim 1, wherein the first active region is arranged at a first location along the first surface disposed a first distance from an upstream end of the channel, and the second active region is arranged at a second location along the second surface disposed the first distance from the upstream end of the channel.

11. The fluidic device of claim 1, wherein the first active region is arranged at a first location along the first surface disposed a first distance from an upstream end of the channel, and the second active region is arranged at a second location along the second surface disposed a second distance from the upstream end of the channel, wherein the second distance is greater than the first distance.

12. The fluidic device of claim 1, further comprising at least one first functionalization material arranged over at least a portion of at least one of the first active region or the second active region, wherein the at least one first functionalization material is in fluid communication with the channel.

13. The fluidic device of claim 12, wherein the at least one functionalization material comprises at least one of a specific binding material or a non-specific binding material.

14. The fluidic device of claim 1, further comprising at least one of the following features (i) or (ii):

at least one first functionalization material is arranged over at least a portion of the first active region, wherein the at least one first functionalization material is in fluid communication with the channel, and a first self-assembled monolayer is arranged between the at least one first functionalization material and the first proximal electrode; or (ii) at least one second functionalization material is arranged over at least a portion of the second active region, wherein the at least one second functionalization material is in fluid communication with the channel, and a second self-assembled monolayer is arranged between the at least one second functionalization material and the second proximal electrode.

15. The fluidic device of claim 1, further comprising at least one of the following features (i) or (ii):

(i) at least one first functionalization material is arranged over at least a portion of the first active region, wherein the at least one first functionalization material is in fluid communication with the channel, a first self-assembled monolayer is arranged between the at least one first functionalization material and the first proximal electrode, a first interface layer is arranged between the first self-assembled monolayer and the first proximal electrode, and a first hermeticity layer is arranged between the first interface layer and the first proximal electrode; or (ii) at least one second functionalization material is arranged over at least a portion of the second active region, wherein the at least one second functionalization material is in fluid communication with the channel, a second self-assembled monolayer is arranged between the at least one second functionalization material and the second proximal electrode, a second interface layer is arranged between the second self-assembled monolayer and the second proximal electrode, and a second hermeticity layer is arranged between the second interface layer and the second proximal electrode.

16. The fluidic device of claim 1, further comprising at least one of (i) a plurality of first bulk acoustic wave resonator structures arranged between the first substrate and the first surface, or (ii) a plurality of second bulk acoustic wave resonator structures arranged between the second substrate and the second surface.

17. A method for fabricating a fluidic device, the method comprising:

fabricating a first bulk acoustic wave resonator structure;
fabricating a second bulk acoustic wave resonator structure; and
arranging at least one intermediate layer defining lateral boundaries of a channel arranged to receive a fluid between the first bulk acoustic wave resonator structure and the second bulk acoustic wave resonator structure;
wherein the first bulk acoustic wave resonator structure comprises a first surface bounding the channel, the second bulk acoustic wave resonator structure comprises a second surface bounding the channel, and the second surface opposes the first surface.

18. The method of claim 17, wherein:
the first bulk acoustic wave resonator structure is arranged between a first substrate and the first surface bounding the channel, wherein the first bulk acoustic wave resonator structure includes a first piezoelectric material, a first distal electrode arranged between the first piezoelectric material and the first substrate, and a first proximal electrode arranged between the first piezoelectric material and the channel, wherein at least a portion of the first piezoelectric material is arranged between the first distal electrode and the first proximal electrode to form a first active region;
the second bulk acoustic wave resonator structure is arranged between a second substrate and a second surface bounding the second channel, wherein the second bulk acoustic wave resonator structure includes a second piezoelectric material, a second distal electrode arranged between the second piezoelectric material and the second substrate, and a second proximal electrode arranged between the second piezoelectric material and the channel, wherein at least a portion of the second piezoelectric material is arranged between the second distal electrode and the second proximal electrode to form a second active region; and
the method further comprises applying at least one functionalization material over at least a portion of at least one of the first active region or the second active region, wherein the at least one functionalization material is in fluid communication with the channel.

19. The method of claim 18, further comprising forming at least one self-assembled monolayer over at least a portion of the first active region or the second active region, wherein the at least one functionalization material is applied over the at least one self-assembled monolayer.

20. The method of claim 19, further comprising forming at least one interface layer over at least a portion of the first active region or the second active region, wherein the at least one self-assembled monolayer is formed over the at least one interface layer.

* * * * *